US005488037A

United States Patent [19]
Sall et al.

[11] Patent Number: 5,488,037
[45] Date of Patent: Jan. 30, 1996

[54] ANTITHROMBOTIC AGENTS

[75] Inventors: Daniel J. Sall; Robert T. Shuman, both of Greenwood, Ind.

[73] Assignee: Eli Lilly and Company, Indianapolis, Ind.

[21] Appl. No.: 206,499

[22] Filed: Mar. 4, 1994

[51] Int. Cl.$^6$ .................. A61K 38/00; C07D 417/00; C07D 279/10; C07D 279/12
[52] U.S. Cl. .................. 514/19; 544/55; 544/58.5; 544/60; 544/96; 544/111; 544/224; 544/242; 546/208; 548/953
[58] Field of Search .................. 514/19; 544/55, 544/58.5, 60, 96, 111, 224, 242; 546/208; 548/953

[56] References Cited

U.S. PATENT DOCUMENTS

| | | | |
|---|---|---|---|
| 4,316,889 | 2/1982 | Bajusz et al. | 424/177 |
| 4,346,078 | 8/1982 | Bajusz et al. | 424/177 |
| 4,399,065 | 8/1983 | Bajusz et al. | |
| 4,478,745 | 10/1984 | Bajusz et al. | |
| 4,703,036 | 10/1987 | Bajusz et al. | 514/18 |
| 5,053,392 | 10/1991 | Klein et al. | 514/18 |
| 5,153,176 | 10/1992 | Abe et al. | 514/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |
| 5,380,713 | 1/1995 | Balasubramaniam et al. | 514/18 |

FOREIGN PATENT DOCUMENTS

| | | |
|---|---|---|
| 293881 | 12/1988 | European Pat. Off. |
| 410411 | 1/1991 | European Pat. Off. |
| 479489 | 4/1992 | European Pat. Off. |
| 526877 | 8/1992 | European Pat. Off. |
| 503203 | 9/1992 | European Pat. Off. |
| 504064 | 9/1992 | European Pat. Off. |
| 530167 | 3/1993 | European Pat. Off. |
| 529568 | 3/1993 | European Pat. Off. |
| 542525 | 5/1993 | European Pat. Off. |
| WO93/08211 | 4/1993 | WIPO. |
| WO93/11152 | 6/1993 | WIPO. |

OTHER PUBLICATIONS

Bajusz, S., et al., *J. Med. Chem.,* 1990, 33, 1729–1735.
Fareed, J., et al., *Annals N.Y. Academy of Sciences,* 1981, 765–784.
Shuman, et al., Proceedings of the Twelfth American Peptide Symposium, Jun. 16–21, 1991, pp. 799–802.
Wilson, et al., American Heart Association, Nov. 11–14, 1991, Anaheim Convention Center, Anaheim, CA., Abstract.
Bajusz, et al., *Int. J. Peptide Res.,* 12, 1978, 217–221.
Gesellschen, et al., Tenth American Peptide Symposium, May 23–28, 1987, St. Louis, Mo.
Claeson, et al., Proceedings of the Twelfth American Peptide Symposium, Jun. 16–21, 1991, Cambridge, MA., 824–825.
Smith, G. F., Shuman, R. T. Gesellchen, P. D. Craft, T. J., Gifford, P., Kurz, K. D. Jackson, C. V., Sandusky, G. E., and P. D. Williams, A New Family of Thrombin Inhibitors with Improved Specificity and Therapeutic Index. (Submitted to the American Heart Association, Oct., 1991, Circulation Oct., 1991, vol. 84, II–579, 1991).
Jackson, V., Wilson, H., Frank J., Crowe, V., Craft, T., and G. Smith. The Thrombin Inhibitor, Methyl–D–Phe–Pro–Arginal—An Effective Adjunct to Coronary Artery Thrombolysis in the Anesthetized Dog. FASEB J. 5(4)A521 (1991), #865.
Crowe, V., Frank J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Cornary Thrombosis. FASEB J. 5(4)A521 (1991), Abstract.
Wilson, H., Frank J., Crowe, V., Coffman, B., Smith, G., Shuman, R., and V. Jackson. Anticoagulant and Antithrombotic Efficacy of the Novel Thrombin Inhibitor, Methyl–D–Phg–Pro–Arginal, in a Canine Model of Coronary Thrombosis (Arteriosclerosis and Thrombsosi, 11(5), Oct., 1991), p. 1586a.
Jackson, V., Wilson, H., Frank, J., Crowe, V., Coffman, B., Shuman, R., and G. Smith. The Novel Thrombin Inhibitor Methyl–D–Phg–Pro–Arginal: An Effective Conjunctive Agent to Coronary Artery Thrombolysis in the Anesthetized Dog. (Arteriosclerosis and Thrombosis, 11(5), Oct., 1991), p. 1586a.
Shuman, R. T., Rothenberger, R. B., Campbell, C. S., Smith, G. F., Jackson, C. V., Kurz, K. D., and P. D. Gesellchen. Prevention of Reocclusion by a Thrombin Inhibitor. (American Peptide Symposium, Jun., 1991, pp. 799–800).
Shuman, R. T., Rothenberger, R. B., Campbell, C. S. Smith, G. F., Jackson, C. V., Kurz, K. D., and P. D. Gesellchen. A Series of Highly Active Serine Proteinase Inhibitors. (American Peptide Symposium, Jun. 1991, pp. 801–802).
Jackson, C. V., Frank, J. D., Crowe, V. G., Craft, T. J., and G. F. Smith. Assessment of the Anticoagulant and Antithrombotic Efficacy of the Thrombin Inhibitor, BOC–Phe–Pro–Arginal, in a Canine Model of Coronary Thrombosis. *Arteriosclerosis,* 10 922A (1990), Abstract.
Jackson, C. V., Frank, J. D., Crowe, V. G., Craft, T. J., and G. F. Smith. The Thrombin Inhibitor, BOC–D–Phe–Pro–Arginal. An Effective Adjunct to Coronary Artery Thrombolysis in the Anesthetized Dog. *Arteriosclerosis,* 10 923a (1990), Abst.
Shackelford, K. A., Tanzer, R. L., Shuman, R., Gesellchen, P. D., Grindey, G. B., Sundboom, J. L., Smith, G. F., and R. L., Merriman. Inhibition of Spontaneous Metastasis by Boc–D–Phe–Pro–Arginal. American Association for Cancer (List continued on next page.)

*Primary Examiner*—Jill Warden
*Assistant Examiner*—Sheela J. Huff
*Attorney, Agent, or Firm*—Thomas E. Jackson; John C. Demeter; David E. Boone

[57] ABSTRACT

This invention relates to L-Arginine aldehyde derivatives, pharmaceutical formulations containing those compounds and methods of their use as thrombin inhibitors, coagulation inhibitors and thromboembolic disorder agents.

35 Claims, No Drawings

OTHER PUBLICATIONS

Research, San Francisco, 1989. *Proc. Am. Assn. Cancer Res.*, 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund–Wistar (LW) Rats to Anti–Fibrin Agents. American Association for Cancer Research. New Orleans, May 1988, *Proc. Am. Assn. Cancer Res.*, 29 240 (1988) Abst.

Neubauer, B. L., Best, K. L., Gesellchen, P. D., Goode, R. L., Merriman, R. L., Tanzer, L. R., Shaar, C. J., Shuman, R., Sundboom, Pro–Arginal on the Metastasis of the PAIII Prostatic Adenocarcinoma in Male Lobund Wistar (LW) Rats. American Urological Association. Boston, May 1988, *J. Urol.*, 139 175A (1988) #49.

Gescellchen, P. D., Smith, G. F., et al., Anticoagulant, Antithrombotic, and Antimetastatic Effects of a Serine Proteinase Inhibitor. 10th American Peptide Symposium, Washington University, St. Louis, MO. (1987), Abst.

Smith, G. F., Sundboom, J. L., Best, K., Gesellchen, P. D., Merriman, R. L., Shuman, R., and Neubauer, B. L. Heparin, Boc–D–Phe–Pro–Arginal, and Warfarin (Fibrin Antagonists) Inhibit Metastasis in an *In Vivo Model.* American Chemical Society National Meeting. Abstract BIOL 70 Biochemistry (1987) Abst.

K. D. Kurz, T. Smith, R. A. Moore, and B. W. Main. Comparison of Thrombin Inhibitors in Rat Models of Thrombosis and Thrombolysis. FASEB Journal, vol. 5, (No. 4), 1991, Abst. #886.

Tomori, et al., *Chromatographia*, vol. 19, 437–442 (1984).

Dayhoff, *Atlas of Protein Sequence and Structure*, 5, pp. 85–89 (1972).

Shuman, et al., *J. Med. Chem.*, 36(3), 314–319 (1993).

Jackson, et al., *J. Cardiovasc. Pharmacol.*, 21(4), 587–594 (1993).

Cheng, et al., *Tetrahedron Lett.*, 32(49), 7333–7336 (1991).

Bagdy, et al., *Thrombosis and Haemostasis*, 68(2), 125–129 (1992).

*Thrombosis and Haemostatic*, 65, 1289, Nos. 2150–2151 and 2512 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem., 36, 300–303 (1993).*

Shuman, et al., Oral Activity of Tripeptide Aldehyde Thrombin Inhibitors, Thirteenth American Peptide Symposium, Jun. 20–25, 1993, Abst.

Kurz et al., Antithrombotic Efficacy in the Rat After Intravenous and Oral Administration of a Direct Inhibitor of the Thrombin FASEB, Mar. 28–Apr. 1, 1993.

Iwanowicz, et al., *Bioorg. Med. Chem. Lett.* 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmacologist*, 35(3), 207 (1993) Abst.

Pozagay, et al., Study of the Specificity of Thrombin with Tripeptidy–p–Nitroanilide Substrate, *Eur. J. Biochem.*, 115, 491–495 (1981).

Jackson, et al., *The Journal of Pharmacology and Experimental Therapy*, 261(2), 546–552 (1992).

Stueber, et al., Proceedings of the 13th American Peptide Symposium, Jun. 20–25, 1993.

Stürzebecher, et al., XIVth Congress of the International Society on Thrombosis and Hemostasis, Jul. 4–9, 1993.

Simoons et al., *Circulation*, 90, I–231, Abstr. 1241 (1994).

ANTITHROMBOTIC AGENTS

BACKGROUND OF THE INVENTION

This invention relates to thrombin inhibitors which are useful anticoagulants in mammals. In particular it relates to L-Arginine aldehyde derivatives having high anticoagulant activity, antithrombotic activity, and oral bioavailability.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins.

Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the post-translational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al., *J. Med, Chem.*, 36, 314–319 (1993).

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, and do not interfere with lysis of blood clots, as required to maintain hemostasis.

The present invention is directed to the discovery that the compounds of the present invention, as defined below, are potent thrombin inhibitors.

Accordingly, it is a primary object of the present invention to provide novel L-arginine aldehyde derivatives that are potent thrombin inhibitors useful as anticoagulants.

Other objects, features and advantages will be apparent to those skilled in the art from the following description and claims.

SUMMARY OF THE INVENTION

The present invention provides thrombin inhibiting compounds having the formula

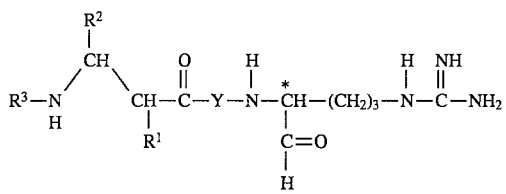

wherein $R^1$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–$C_4$)alkyl, or cyclohexyl($C_1$–$C_4$)alkyl;

$R^2$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl ($C_1$–$C_4$)alkyl or cyclohexyl($C_1$–$C_4$)alkyl;

$R^3$ is hydrogen, $C_1$–$C_4$ alkyl or ($C_1$–$C_4$ alkyl)S(O)$_n$ where n is 1 or 2;

$R^1$ and $R^2$, with the carbon atoms to which they are bonded, are combined to afford a 5 or 6 membered cycloalkyl group, a phenyl group or norbornanyl group;

$R^2$ and $R^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

$R^1$, $R^2$ and $R^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or an unsubstituted or substituted 9 or 10 membered nitrogen containing heterocyclic ring which may further contain another hetero atom selected from nitrogen, oxygen and sulfur;

Y is

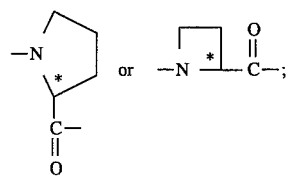

and pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

In addition to the compounds of formula I, the present invention provides pharmaceutical formulations comprising a compound of formula I in association with a pharmaceutically acceptable carrier, diluent or excipient.

The present invention also provides a method of inhibiting coagulation in mammals comprising administering to a mammal in need of treatment, a coagulation inhibiting dose of a compound of formula I.

The present invention further provides a method of inhibiting thrombin comprising administering to a mammal in need of treatment, a thrombin inhibiting dose of a compound of formula I.

Further, the present invention provides a method of treating thromboembolic disorders comprising administering to a mammal requiring treatment, an effective dose of a compound of formula I.

DETAILED DESCRIPTION OF THE INVENTION

This invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent, unless otherwise stated means a straight or branched chain alkyl radical having the stated number of carbon atoms such as methyl, ethyl, n-propyl, isopropyl, n-butyl, t-butyl, isobutyl and sec-butyl.

The term "alkoxy" means a straight or branched chain alkyl radical having the stated number of carbon atoms bonded to the parent moiety by an oxygen atom. The term "halo" means chloro, fluoro, bromo or iodo. The term "di($C_1$–$C_4$ alkyl) amino" means a group —N($C_1$–$C_4$ alkyl)$_2$ where each alkyl group, independently, has the stated number of carbon atoms.

The term "phen($C_1$–$C_4$)alkyl" means a straight chain alkyl radical having the stated number of carbon atoms with a phenyl ring bond to the terminal carbon atom of the alkyl radical.

The term "cyclopentyl($C_1$–$C_4$)alkyl" means a straight chain alkyl radical having the stated number of carbon atoms with a cyclopentyl ring bonded to the terminal carbon atom of the alkyl radical.

The term "cyclohexyl($C_1$–$C_4$)alkyl" means a straight chain alkyl radical having the stated number of carbon atoms with a cyclohexyl ring bonded to the terminal carbon atom of the alkyl radical.

The term "norbornanyl" means a group having the structure

where —NHR$^3$ are the same amino group drawn in Formula I.

A substituted phenyl and substituted phen($C_1$–$C_4$)alkyl can have one or two of the same or different substitutents on the phenyl ring selected from halo, hydroxy, $C_1$–$C_4$ alkyl, $C_1$–$C_4$ alkoxy, amino (—NH$_2$), and $C_1$–$C_4$ alkylamino.

The term "5 or 6 membered nitrogen containing heterocycle ring" means any 5 or 6 membered nitrogen containing ring that will afford a stable structure containing one nitrogen atom that may further contain one nitrogen atom, one sulfur atom, or one oxygen atom. Heterocyclics include pyrazolyl, oxazolyl, isoxazoly, thiazoly, isothiazolyl, pyranyl, pyrinidinyl, pyrazinyl, and oxazinyl.

The term "9 or 10 membered nitrogen containing heterocyclic ring" means any bicyclic group in which any of the above 5 or 6 membered rings is fused to a benzene ring, cyclohexane ring or another heterocyclic ring that will afford a stable structure. These heterocyclics include, but are not limited to, indolyl, benzothienyl, benzofuryl, benzoxazolyl, benzoisoxazolyl, benzopyrazoly, quinolinyl, isoquinolinyl, benzimidozolyl and benzothiazolyl. Some of the above heterocycles may exist in tautomeric forms. All such form are included within the scope of this invention.

When R$^2$ and R$^3$ or R$^1$, R$^2$ and R$^3$, with the respective carbon and nitrogen atoms to which they are bonded, combine to afford a stable substituted 5 or 6 membered nitrogen containing heterocyclic ring which may further contain another hereto atom selected from nitrogen, oxygen and sulfur, or a stable substituted 9 or 10 membered nitrogen containing heterocyclic ring which may further contain another hetero atom selected from nitrogen, oxygen and sulfur, there are one or two substituents selected from halo, hydroxyl, $C_1$–$C_4$ alkyl, $C_1$–$C_4$ alkoxy, amino (—NH$_2$), mono($C_1$–$C_4$ alkyl)amino, di($C_1$–$C_4$ alkyl)amino, mercapto, ($C_1$–$C_4$ alkyl)thio (—S(O)$_p$$C_1$–$C_4$ alkyl), —NHS(O)$_p$($C_1$–$C_4$ alkyl), —NHC(O)$C_1$–$C_4$ alkyl, —S(O)$_p$NH$_2$, —S(O)pNH($C_1$–$C_4$ alkyl), and —S(O)$_p$N($C_1$–$C_4$ alkyl)$_2$, and p is 1 or 2;

The groups

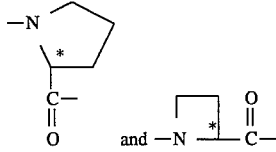

are referred to as prolinyl and azetidine-2-carbonyl, respectively, and are respectively abbreviated Pro and Azt.

In the representation of Formula I, the carbonyl functionality of group Y is attached to the amino group drawn in Formula I. The amino functionality of Y is attached to the carbonyl group drawn in Formula I.

The above heterocycles may exist in tautomeric forms. All such forms are included within the scope of this invention.

The asterisks in formula I and substituent Y denote a chiral center that is (L).

In addition, diastereomers may exist at the carbon atoms to which the R$^1$ and R$^2$ substituents are bonded depending on substitutions. The compounds of the present invention include mixtures of two or more diastereomers as well as each individual isomer.

Preferred compounds of the present invention are those compounds of formula I where:

R$^1$ is hydrogen, phen($C_1$–$C_4$)alkyl, or cyclohexyl($C_1$–$C_4$) alkyl;

R$^2$ is hydrogen, cyclopentyl, cyclohexyl or phenyl;

R$^3$ is hydrogen or $C_1$–$C_4$ alkyl; or

R$^1$ and R$^2$, with the carbon atoms to which they are bonded, are combined to afford a 5 or 6 membered cycloalkyl group; or R$^1$, R$^2$ and R$^3$, with respective carbon and nitrogen atoms to which they are bonded, are combined to afford an unsubstituted or substituted 9 or 10 membered nitrogen containing heterocyclic ring; and Y is as defined above for formula I and pharmaceutically acceptable salts and solvates thereof; provided that when Y is prolinyl, R$^1$ is hydrogen and R$^3$ is hydrogen, R$^2$ is not phenyl; and further provided that when Y is prolinyl, R$^2$ is hydrogen and R$^3$ is hydrogen, R$^1$ is not benzyl.

Particularly preferred compounds of the present invention are those compounds of formula I where:

R$^1$ is hydrogen, benzyl or cyclohexylmethyl;

$R^2$ is hydrogen, cyclohexyl or phenyl;
$R^3$ is hydrogen or $C_1$–$C_3$ alkyl; or
$R^1$ and $R^2$, with the carbon atoms to which they are bond, are combined to afford a 5 or 6 membered cycloalkyl group; and Y is as defined above for formula I; and pharmaceutically acceptable salts or solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

As mentioned above, the invention includes pharmaceutically acceptable salts of the compounds defined by the above formula I. A particular compound of this invention can possess one or more sufficiently basic functional groups, and accordingly react with any of a number of nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, subcrate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

As stated above, the present invention includes solvates of the compounds of Formula I and the pharmaceutically acceptable salts therein. A particular compound of the present invention or a pharmaceutically acceptable salt thereof may form solvates with water or common organic solvents. Such solvates are included within the scope of compounds of the present invention.

The compounds of Formula I are prepared by known methods of peptide coupling. According to one such method the acid PX-COOH, where X is $R^3$—NH—CHR$^2$—CHR$^1$, where $R^1$, $R^2$, and $R^3$ are as defined above for Formula I, and P is an amino protecting group, is coupled with a carboxy protected proline (or azetidine-2-carboxy ester) to form the dipeptide. The carboxy protecting ester group of the proline moiety is then removed (deblocked or deesterified) and the free acid form of the dipeptide is coupled with the lactam form of arginine. The above reaction sequence is illustrated by the following Scheme 1:

PX—COOH + proline ester 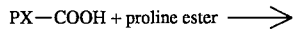

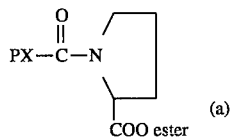

(a) $\xrightarrow{\text{deesterify}}$ PX—(C=O)—Pro—OH (b)

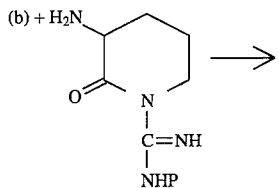

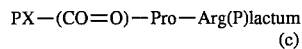
PX—(CO=O)—Pro—Arg(P)lactum
(c)

wherein P represents an amino protecting group.

The coupled Arg(P) lactam product (c) is reacted with a hydride reducing agent, preferably lithium aluminum hydride or lithium tritert-butoxyaluminohydride in an inert solvent or mixture of solvents to reduce the lactam ring and provide the tripeptide in the arginine aldehyde form represented by the formula

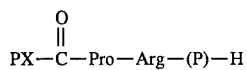

wherein (P) represents amino protecting groups.

The protecting groups are removed by procedures known to those skilled in the art such as hydrogenation over a metal catalyst.

The lactam form of arginine is obtained by intramolecular coupling of amino protected arginine [Arg-OH]. For example, Boc-Arg(Cbz)OH represented by the formula

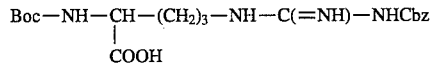

where Boc is t-butyloxycarbonyl and Cbz is benzyloxycarbonyl is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the di-amino protected arginine as shown below

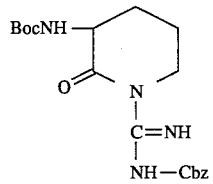

Prior to use in the coupling with the PX(C=O)—Pro—OH as shown in the above scheme, the Boc or other amine protecting group is selectively removed with trifluoroacetic acid or HCl to provide the requisite free amino group.

The coupling of an PXCOOH compound with a proline ester, when X is $R^3$—NH—CHR$^2$—CHR1— where $R^1$, $R^2$ and $R^3$ are as defined above for formula I, is carried out by first protecting the amino group of the amino acid. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth- 1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichlorethoxycarbonyl, 2-ethynyl-2-propoxycarbonyl, cyclopropylmethoxycarbonyl, 4-(decyloxy)benzyloxycarbonyl, isobornyloxycarbonyl, 1-piperidylcarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the conditions of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction an ester protecting group for proline is employed which is removable by conditions under which the amino protecting group remains intact. The amino protecting group of the acylating acid PXCOOH thus remains in place for protection of the amino group during the subsequent coupling with the arginine lactam compound to form c in Scheme 1.

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$–$C_3$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, 2-(trimethylsilyl)ethyl, 2-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Preferred carboxy protecting groups are $C_1$–$C_3$ alkyl and benzyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of Formula I where Y is azetidinyl (or prolinyl) are prepared in an analogous manner by known methods of peptide coupling. According to one such method, the cyclic lactam form of arginine (e) is prepared and coupled with an amino protected azetidine-2-carboxylic acid (d) as shown below to afford the dipeptide (f)

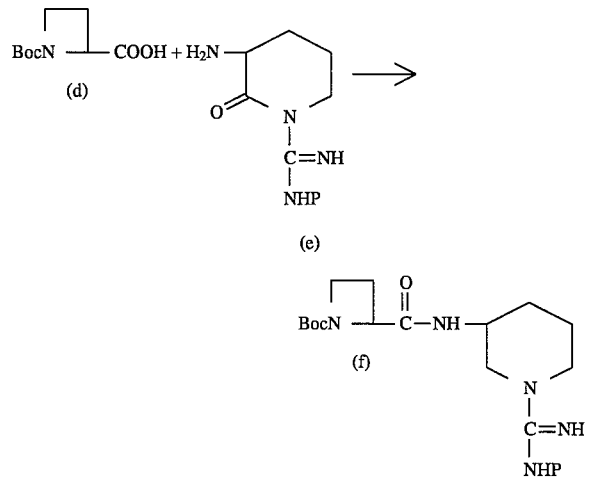

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and P. G. M. Wuts, Chapter 7, page 309–405 (1991), John Wiley & Sons, Inc., publishers, incorporated herein by reference in its entirety. The Boc, or other suitable protecting group, is removed from the azetidine ring nitrogen which is then acylated with the desired amino acid acyl group to afford the tripeptide shown below.

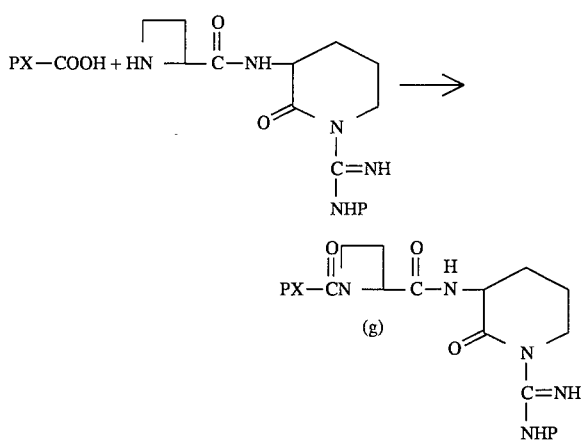

Although illustrated and described for those compounds of the present invention where Y is azetidinyl-2-carbonyl, one skilled in the art will appreciate these procedures can also be used to afford those compounds of the present invention where Y is prolinyl.

The coupled Arg(P) lactam product (g) is reduced with a hydride reducing agent, preferably lithium aluminum hydride or lithium tri-tert-butoxyaluminohydride in an inert solvent or mixture of solvents to reduce the lactam and provide the tripeptide in the arginine aldehyde form represented by the formula PX(C=O)—Azt—Arg(P)—H wherein P represents an amino protecting group. The protecting groups are removed by procedures known to those skilled in the art such as hydrogenation over a metal catalyst.

Alternatively, the compounds of the invention are prepared by coupling the PXCOOH acid with carboxy protected azetidine-2-carboxylic acid. The dipeptide is deprotected then coupled with the amino protected arginine in the lactam form prepared as described above. The tripeptide is then reduced to open the lactam ring and provide the amino protected arginal tripeptide as described above.

The coupling of an PXCOOH compound is carried out by first protecting the amino group of the amino acid. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

The compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of formula I, while at the same time preparing a desired stable salt form, is that described in U.S. Pat. No. 5,250,660, incorporated by reference herein. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form e.g. Bio-Rad AG-1X8. After adjustment of the pH, the solution of tripeptide sulfate or hydrochloride salt is lyophilized to provide the pure salt in dry powder form. In an example of the process, crude 2-aminocyclohexylcarbonyl-L-Pro-L-Arg-H hydrochloride is dissolved in water and the solution is loaded on Vydac $C_{18}$ RP-HPLC 5 cm×50 cm column. A gradient of 2–20% B (A=0.01% $H_2SO_4$; B= acetonitrile) over 10 hours is used. Multiple fractions are collected and those containing product as determined by analytical RP-HPLC are pooled. The pH of the pooled fractions is adjusted to pH 4.0–4.5 with AG-1X8 resin in hydroxide form (Bio-Rad, 3300 Ragatta Blvd., Richmond, Calif. 94804). The solution is filtered and the filtrate is lyophilized to provide the pure L-,L-, tripeptide in the form of the hydrochloride salt.

The optically active isomers of the diastereomers of the $R^3$—NH—$CHR^2$—$CHR^1$-radical are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe the invention and are not to be construed as limitations thereof.

The analytical HPLC methods used in the examples were as follows:

Method 1. Hitachi L-6200 using a Vydac $C_{18}$ reversed-phase column of 0.46 cm×10 cm. Samples were eluted using a gradient composed of A (0.1% (v:v) aqueous TFA) and B (0.1% (v:v) TFA in acetonitrile). The chromatogram was monitored at 214 nm using a L-4000 UV detector.

The abbreviations used in the examples have the following meanings.

Amino acids: Arg=arginine, Pro=proline, Azt= azetidine-2-carbonyl
Boc=t-butyloxycarbonyl (t-butoxycarbonyl)
Bzl=benzyl
cbz=benzyloxycarbonyl
DCC=dicyclohexylcarbodiimide
DMF=dimethylformamide
DMSO=dimethylsulfoxide
EtOAc=ethyl acetate
$Et_2O$=diethyl ether
EtOH=ethanol
FAB-MS=fast atom bombardment mass spectrum FD-MS=field desorption mass spectrum
HOBT=1-hydroxybenzotriazole hydrate
HPLC=High Performance Liquid Chromatography
IR=Infrared Spectrum
LAH=Lithium Aluminum Hydride
NMR=Nuclear Magnetic Reasonance
MOC=methoxycarbonyl
RPHPLC=Reverse Phase High Performance Liquid Chromatography
TFA=trifluoroacetic acid
THF=tetrahydrofuran
TLC=thin layer chromatography Unless otherwise stated, pH adjustments and work up are with aqueous acid or base solutions.

EXAMPLE 1

Preparation of N-methyl-3-amino-3-phenylpropionyl-L-Prolinyl-L-Arginine Aldehyde Dihydrochloride Dihydrate A. D,L-N-Cbz-3-amino-3-phenyl propionic acid.

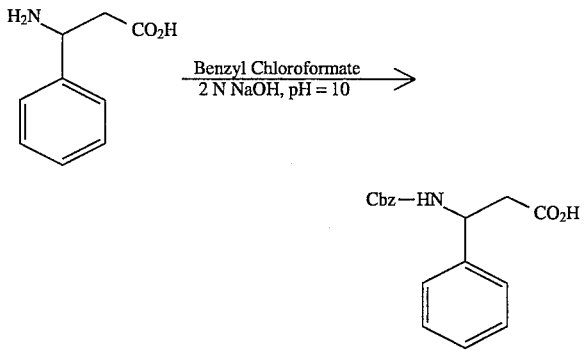

A 0° C. slurry of 50.0 g (300 mmole) of DL-3-amino-3-phenyl propionic acid in 300 mL of 1N aq NaOH (300 mmole) was treated simultaneously with 48.0 mL (340 mmole) of benzyl chloroformate and 300 mL of 1N aq NaOH (300 mmole). The reaction was stirred at ambient temperature for 18 h at which time the reaction was acidified to pH 2 with conc. aq HCl and extracted with EtOAc (4×200 mL). The combined organic fractions were dried over $Na_2SO_4$ and evaporated in vacuo to give 73.4 g (250 mmol; 82%) of N-Cbz-3-amino-3-phenyl propionic acid as an off white solid.

FD-MS, m/e 299 (M$^+$, 100).
IR (KBr) 3362, 3038, 1697, 1532, 1289, 1231, 1028, 699 cm$^{-1}$.
Analytical Calculated for $C_{17}H_{17}NO_4$: C 68.22, H 5.72, N 4.68
Found: C 68.51, H 5.81, N 4.90

B. D,L-N-methyl-N-cbz-3-amino-3-phenyl propionic acid.

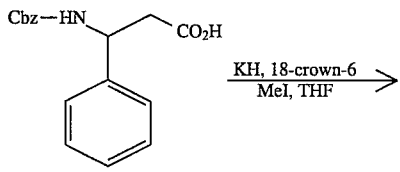

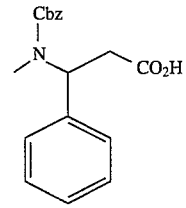

A solution of 22.8 g (76 mmol) of N-Cbz-3-amino-3-phenyl propionic acid in 50 mL THF was added to a 0° C. slurry of 36.6 g (230 mmole; 25% suspension in mineral oil) of KH and 1.0 g (4 mmol) of 18-crown-6 at a rate that kept the reaction temp below 10° C. A solution of MeI (86.3 g; 610 mmol) in 50 mL THF was added dropwise and the reaction stirred at 10° C. for 3 h. The reaction was quenched with 15 mL of acetic acid and was poured into 200 mL $H_2O$. The aqueous pool was adjusted to pH 10 with 5N aq NaOH and washed with $Et_2O$ (2×100 mL). The aqueous layer was acidified to pH 4 with 5N aq HCl and extracted with EtOAc (4×200 mL). The combined EtOAc layers were dried over $MgSO_4$ and evaporated in vacuo to give 15.6 g of an orange oil which was purified by flash chromatography ($SiO_2$; 5% MeOH in $CHCl_3$) to afford 10.5 g (33.5 mmol; 45%) of N-methyl-N-Cbz-3-amino- 3-phenyl propionic acid as a clear oil.

$^1$H NMR ($CDCl_3$) δ 10.05-7.90 (broad, 1H), 5.95-5.78 (m, 1H), 5.20 (s, 2H), 3.04 (d, J=6.7 Hz), 2.74 (s, 3H).
FD-MS m/e 313 (M$^+$, 100).

C. N-Methyl-N-Cbz-3-amino-3-phenyl propionyl-L-Pro-benzyl ester.

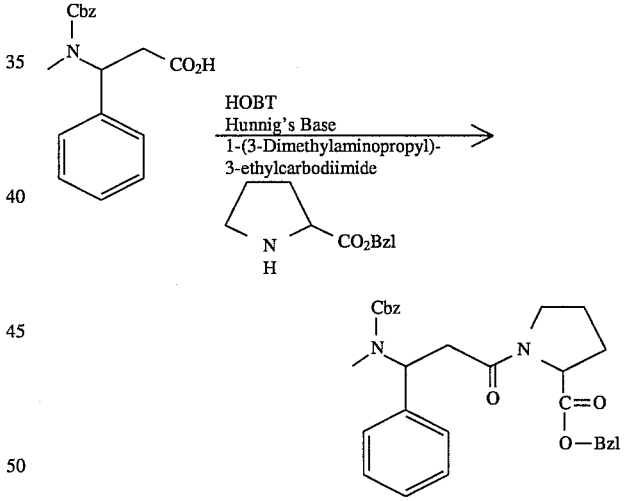

A 5° C. solution of 10.5 g (33.5 mmol) of N-methyl-N-cbz- 3-amino-3-phenyl propionic acid, 8.12 g (33.5 mmol) of L-proline benzylester, and 4.53 g (33.5 mol) of 1-hydroxybenzotriazole hydrate in 300 mL of THF was treated with 12.96 g (100 mmol) of diisopropylethylamine and 7.08 g (36.9 mmol) of 1-( 3-dimethylaminopropyl)-3-ethylcarbodiimide hydrochloride. The mixture was stirred at 5° C. for 30 min and allowed to warm to ambient temperature over 66 hrs. The solvent was evaporated in vacuo and the residue diluted with 500 mL of EtOAc. The mixture was washed successively with 1N aq. HCl (2×), sat'd aq. $NaHCO_3$ (2×), and brine. The organic layer was dried over $Na_2SO_4$ and evaporated in vacuo to give a colorless oil which was purified by flash chromatography ($SiO_2$; 10% EtOAc in $CH_2Cl_2$) to afford 12.88 g (25.8 mmol; 77%) of N-methyl- N-Cbz-3-amino-3-phenyl propionyl-L-Pro-benzyl ester as a clear oil.
IR (CHCl$_3$) 3025, 3019, 3013, 1741, 1690, 1645, 1453 cm$^{-1}$.
FD-MS, m/e 500 (M$^+$, 100).
Analytical Calculated for C$_{30}$H$_{32}$N$_2$O$_5$: C 71.98, H 6.44, N 5.60
Found: C 72.11, H 6.54, N 5.60
$[\alpha]_D$=−43.1° (c=0.01, MeOH).

D. N-methyl-N-Cbz-3-amino-3-phenyl propionyl-L-Pro-Arg-N-Cbz lactam.

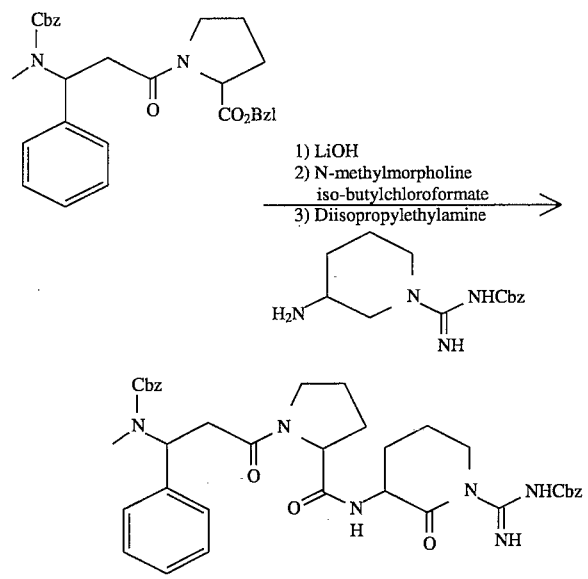

A solution of 12.5 g (25 mmol) of N-methyl-N-Cbz-3-amino- 3-phenyl propionyl-L-Pro-benzyl ester in 200 mL dioxane was treated with 5.23 g (125 mmol) of LiOH followed by 100 mL of H$_2$O. The reaction was stirred at RT for 16 h at which time the dioxane was evaporated in vacuo. The cloudy mixture was diluted with 20 mL H$_2$O and was extracted with CH$_2$Cl$_2$ (2×). The aqueous layer was acidified to pH 2 with 5N aq HCl and was extracted with CHCl$_3$ (3×). The combined chloroform extracts were evaporated in vacuo to give 9.85 g of the crude corresponding acid as a white foam. The presence of the desired product was confirmed by FD-MS (m/e 411, M+1, 100) and the mixture taken on directly to the next reaction.

A −15° C. solution of 9.65 g of the crude acid in 100 mL THF was treated with 2.38 g (23 mmol) of N-methylmorpholine followed by 3.20 g (23 mmol) of isobutylchloroformate. The mixture was stirred for 5 min and was treated with a solution of 8.54 g (23 mmol) of the arg-lactam and 6.07 g (46 mmol) of diisopropylethylamine in 300 mL of a 2:1 mixture of DMF and THF. The reaction was allowed to reach ambient temperature overnight at which time 15 mL of 1N aq. NaHCO$_3$ was added. The solvent was evaporated in vacuo and the resulting oil partitioned between 200 mL EtOAc and 100 mL H$_2$O. The organic layer was separated and was washed successively with 1M aq NaHSO$_4$, H$_2$O, saturated aq NaHCO$_3$, and brine. The organic phase was dried over Na$_2$SO$_4$ and evaporated in vacuo to give a white foam which was purified by flash chromatography (SiO$_2$: 30% CH$_3$CN in CH$_2$Cl$_2$) to afford 6.96 g (10 mmol; 40% from N-methyl-N-Cbz-3-amino-3-phenyl propionyl-L-Pro-benzyl ester) of N-methyl-N-Cbz-3-amino- 3-phenyl propionyl-L-Pro-Arg-N-Cbz lactam as a white foam.
FD-MS, m/e 683 (MH$^+$).
IR (CHCl$_3$) 3373, 3012, 1687, 1614, 1499, 1266, 1180 cm$^{-1}$.

Analytical Calculated for C$_{37}$H$_{42}$N$_6$O$_7$: C 65.09, H 6.20, N 12.31
Found: C 65.31, H 6.37, N 11.85
$[\alpha]_D$=−52.8° (c=0.01, CH$_2$Cl$_2$).

E. N-methyl-3-amino-3-phenyl propionyl-L-Pro-L-Arg-Aldehyde.

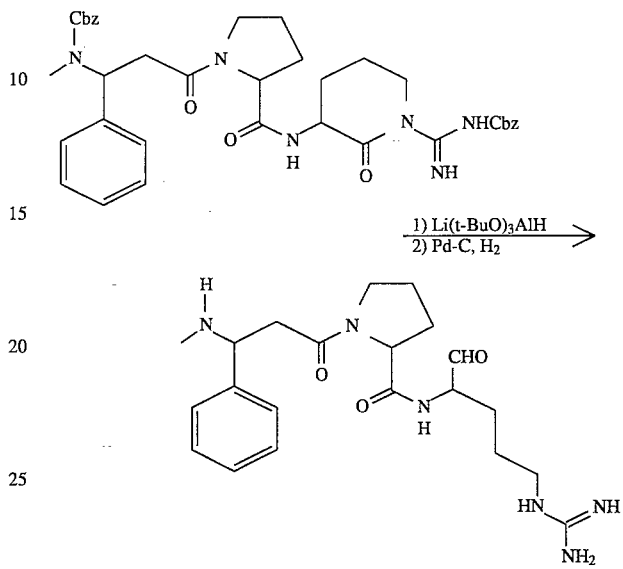

A −25° C. solution of 6.96 g (10 mmol) of N-methyl-N-Cbz- 3-amino-3-phenyl propionyl-L-Pro-Arg-N-Cbz lactam in 120 mL THF was treated with 15 mL (15 mmol; 1M in THF) of Li(t-BuO)$_3$AlH solution at a rate that did not warm the reaction temperature to above −20° C. The reaction was stirred at −25° C. for 2.5 h and was poured into 100 mL of 1N aq HCl. The mixture was extracted with a 1:1 mixture of THF:hexanes (2×300 mL) followed by EtOAc (2×300 mL). The combined EtOAc extracts were dried over Na$_2$SO$_4$ and evaporated in vacuo to give 6.88 g of a white foam. The presence of the desired product was confirmed by FD-MS (m/e 685, M$^+$) and the mixture taken on directly to the next reaction.

A solution of the crude reduction product in 300 mL of EtOH, 100 mL of H$_2$O and 15 mL of 1N aq HCl was charged with 1.7 g of 5% Pd/C and the mixture treated with a stream of H$_2$ gas for 3 h. The catalyst was filtered and washed with 200 mL of a 3:1 EtOH:H$_2$O mixture. The combined filtrates were evaporated in vacuo to 15 mL and diluted back to 75 mL with H$_2$O. The mixture was adjusted to pH 4 with AG 1-X8 anion exchange resin and was lyophilized to afford 3.6 g (6.9 mmol; 69% from N-methyl-N-Cbz- 3-amino-3-phenyl propionyl-L-Pro-Arg-N-Cbz lactam) of N-methyl-3-amino-3-phenyl propionyl-L-Pro-L-Arg-aldehyde dihydrochloride dihydrate.
FAB-MS m/e 417 (MH$^+$, 100).
IR (KBr) 3314, 2958, 1657, 1457, 703 cm$^{-1}$.
Analytical Calculated for C$_{21}$H$_{32}$N$_6$O$_3$·2HCl·2H$_2$O: C 48.00, H 7.29, N 15.99
Found: C 47.54, H 7.04, N 15.92
$[\alpha]_D$=−90.3° (c=0.01, MeOH).

EXAMPLE 2

Preparation of N-methyl-3-amino-3-cyclohexyl propionyl-L-Pro-L-Arg aldehyde dihydrochloride hemihydrate.

A. N-Cbz-3-amino-3-cyclohexyl propionic acid.

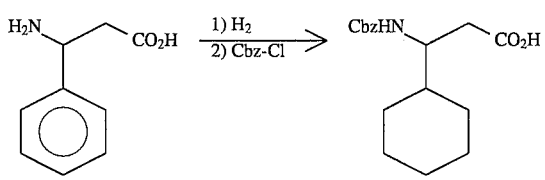

A solution of 25 g (151 mmol) of 3-amino-3-phenylprop-rionate in 450 mL of HOAc was charged with 25 g of 5% Rh/Al$_2$O$_3$ and the mixture hyrogenated at 60 psi for 30 hr at 60° C. The reaction was filtered over celite and evaporated in vacuo to a dark oil. The presence of the desired product was confirmed by FD-MS (m/e 172, MH$^+$, 100). The crude reduction product was treated with benzylchloroformate (25.67 g; 151 mmol) under basic conditions substantially according to the procedures of Example 1, A, to afford 23.4 g of N-Cbz-3-amino-3-cyclohexyl propionic acid as a grey solid.
FD-MS, m/e 306 (MH$^+$; 100)
IR (CHCl$_3$) 3438, 2932, 1715, 1751, 1451 cm$^{-1}$.
Analytical Calculated for C$_{17}$H$_{23}$NO$_4$: C 66.86, H 7.59, N 4.59
Found: C 66.56, H 7.65, N 4.41

B. N-methyl-N-Cbz-3-amino-3-cyclohexyl propionic acid.

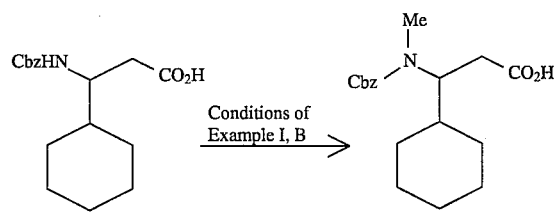

By substantially following the procedures of Example 1, B, 11.0 g (36.07 mmol) of N-Cbz-3-amino-3-cyclohexyl propionic acid was treated with KH and MeI to afford 24.76 g of crude methyl N-methyl-N-Cbz-3-amino-3-cyclohexyl propionate. The methyl ester was hydrolyzed to the corresponding acid substantially according to the procedures of Example 1, D, to afford 7.50 g of N-methyl-N-Cbz-3-amino-3-cyclohexyl propionic acid, as an oil.
FD-MS m/e 320 (MH$^+$, 100)
IR (CHCl$_3$) 3012, 2932, 1698, 1451, 1124, 986 cm$^{-1}$.

C. N-methyl-N-Cbz-3-amino-3-cyclohexyl-L-Pro-benzyl ester.

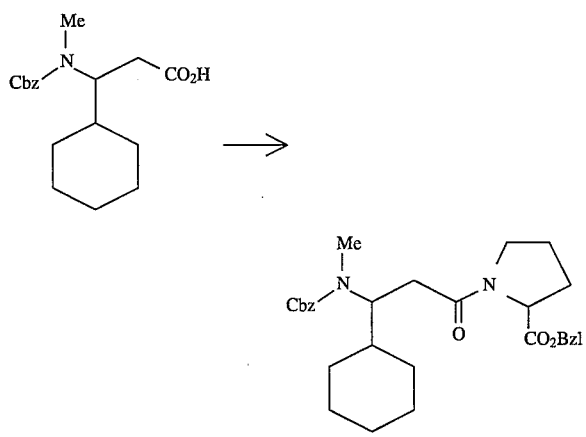

By substantially following the methods of Example 1, C, 8.6 g (27.0 mmol) of N-methyl-N-Cbz-3-amino-3-cyclo-hexyl propionic acid was coupled to L-proline benzyl ester. Purification of the crude product by flash chromatograpy (SiO$_2$; 10% EtOAc in CH$_2$Cl$_2$) afforded 5.80 g (11.5 mmol; 43%) of N-methyl-N-Cbz-3-amino-3-cyclohexyl-L-Pro-benzyl ester as a clear oil.
FD-MS, m/e 507 (MH$^+$; 100)
IR (CHCl$_3$) 3012, 2934, 1742, 1689, 1451, 1172 cm$^{-1}$.
Analytical Calculated for C$_{30}$H$_{38}$N$_2$O$_5$: C 71.12, H 7.56, N 5.53
Found: C 71.30, H 7.61, N 5.69

D. N-methyl-N-Cbz-3-amino-3-cyclohexyl propionyl-L-Pro-Arg-N-Cbz lactam.

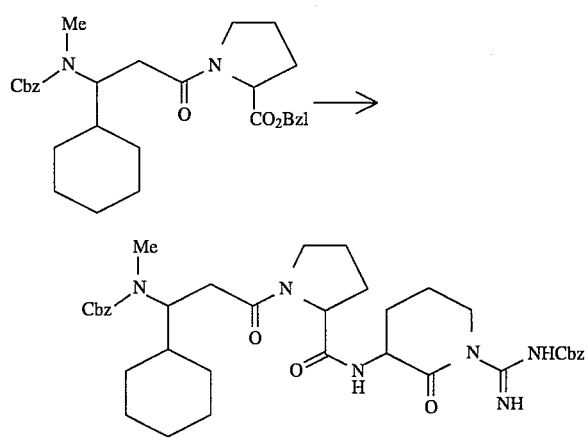

By substantially following the conditions of Example 1, D, 5.37 g (10.6 mmol) of N-methyl-N-Cbz-3-amino-3-cyclohexyl-L-Pro benzyl ester was hydrolyzed to afford 4.36 g of the corresponding acid. The presence of the desired acid was confirmed by FD-MS (m/e 417; M$^+$1, 100) and the crude product coupled to the Cbz-protected arg-lactam (3.80 g; 10.48 mmol). The coupled product was purified by flash chromatography (SiO$_2$; 75% EtOAc in CH$_2$Cl$_2$) to afford 4.24 g (6.17 mmol; 58% from N-methyl-N-Cbz-3-amino-3-cyclohexyl-L-Pro-benzyl ester) of the title compound.
FD-MS, m/e 688 (M$^+$), 511 (100).
IR (CHCl$_3$) 3011, 2935, 1687, 1615, 14989, 1267, 1182 cm$^{-1}$.
Analytical Calculated for C$_{37}$H$_{48}$N$_6$O$_7$: C 64.52, H 7.02, N 12.20
Found: C 64.63, H 7.11, N 12.13
$[\alpha]_D=-51.8°$ (c=0.01, CH$_2$Cl$_2$).

E. N-methyl-3-amino-3-cyclohexyl propionyl-L-Pro-L-Arg Aldehyde.

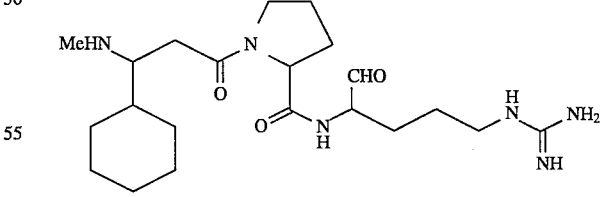

By substantially following the procedures of Example 1, E, 1.83 g (2.66 mmol) of N-methyl-N-Cbz-3-amino-3-cy-clohexyl propionyl-L-Pro-Arg-N-Cbz lactam was reduced with lithium tri-t-butoxyaluminum hydride to afford 1.09 g of the crude protected arginal. Deprotection according to Example 1, E, gave 0.56 g (1.07 mmol; 40% over two steps) of N-methyl-3-amino-3-cyclohexyl propionyl-L-Pro-L-Arg Aldehyde as the dihydrochloride hemihydrate.
FAB-MS, m/e 423 (M$^+$; 100).

IR (KBr) 3347, 2932, 1657, 1450 cm$^{-1}$.
Analytical Calculated for $C_{21}H_{38}N_6O_3 \cdot 2HCl \cdot 0.5H_2O$: C 50.17, H 8.14, N 16.96
Found: C 49.99, H 8.19, N 16.71
$[\alpha]_D = -49.3°$ (c=0.01 MeOH).

EXAMPLE 3

Preparation of N-Methyl-3-amino-2-benzylpropionyl-L-Pro-L-Arg Aldehyde Dihydrochloride Monohydrate.

Ethyl N-Cbz-3-amino-2-benzyl propionate.

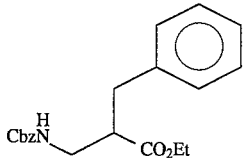

A solution of 21.0 g (103 mmol) of ethyl-2-cyano-3-phenylproprionate in 140 mL of EtOH was charged with 3.0 g of 5% Pd/C and 3.0 g of HCl (g). The resulting mixture was hydrogenated at 60 psi for 3 h at room temperature. The reaction was filtered through Celite® and evaporated to give 25.14 g of a dark viscous oil which was treated with benzylchloroformate (19.34 g; 113 mmol) under basic conditions substantially according to Example 1, A. Purification of the reaction mixture by flash chromatography (SiO$_2$; CH$_2$Cl$_2$) afforded 16.70 g (48.7 mmol; 49%) of ethyl-N-Cbz-3-amino-2-benzyl propionate as a clear oil.
FD-MS, m/e 341 (M$^+$; 100)
IR (CHCl$_3$) 3453, 3029, 1722, 1514, 1196 cm$^{-1}$.
Analytical Calculated for $C_{20}H_{23}NO_4$: C 70.36, H 6.79, N 4.10
Found: C 70.59, H 6.82, N 4.21

N-Cbz-3-amino-2-benzyl propionic acid.

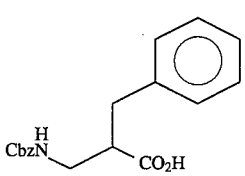

A sample of 16.60 g (48.68 mmol) of ethyl N-Cbz-3-amino- 2-benzyl propionate was hyrdrolyzed substantially according to the conditions of Example 1, D, to afford 14.40 g (46.0 mmol; 94%) of a N-Cbz-3-amino-2-benzyl propionic acid as a white solid.
FD-MS, m/e 313 (M$^+$; 100)
IR (CHCl$_3$) 3022, 1700, 1405, 1142 cm$^{-1}$.
Analytical Calculated for $C_{18}H_{19}NO_4$: C 68.99, H 6.11, N 4.47
Found: C 68.78, H 6.23, N 4.50

C. N-Methyl-N-Cbz-3-amino-2-benzyl propionic acid.

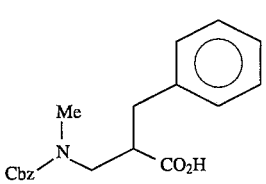

By substantially following the procedures of Example 1, B, 13.90 g (44.4 mmol) of N-Cbz-3-amino-2-benzyl propronic acid, was alkylated to afford 14.23 g of a mixture of the N-methylated carboxylic acid and the N-methylated methyl ester. The crude mixture was hydrolyzed substantially according to the conditions of Example 1, D, to afford 8.10 g of N-methyl-N-Cbz- 3-amino-2-benzyl propionic acid. The presence of the desired product was confirmed by FD-MS (m/e 328, MH$^+$, 100) and the crude material taken on directly to the next reaction.

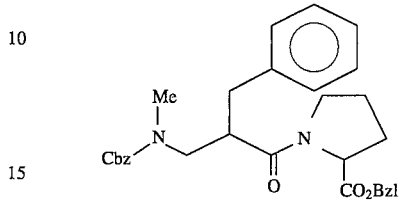

D. N-methyl-N-Cbz-3-amino-2-benzyl propionyl-L-Pro-benzyl ester.

By substantially following the methods described in Example 1, C, 8.07 g of crude N-methyl-N-Cbz-3-amino-2-benzyl propionic acid was coupled to proline benzyl ester. Purification of the reaction mixture by flash chromatography (SiO$_2$, 10% EtOAc in CH$_2$Cl$_2$) afforded 9.0 g (17.5 mmol; 39% from N-methyl-N-Cbz-3-amino-2-benzyl propionic acid) of N-methyl-N-Cbz-3-amino-2-benzyl propionyl-L-Pro-benzyl ester as a clear oil.
FD-MS, m/e 515 (MH$^+$; 100)
IR (CHCl$_3$) 3010, 1742, 1694, 1638, 1451, 1172 cm$^{-1}$.
Analytical Calculated for $C_{31}H_{34}N_2O_5$: C 72.35, H 6.66, N 5.44
Found: C 72.60, H 6.75, N 5.42
$[\alpha]_D = -53.5°$ (c=0.01, MeOH).

E. N-Methyl-N-Cbz-3-amino-2-benzylpropionyl-L-Pro-Arg-N-Cbz lactam

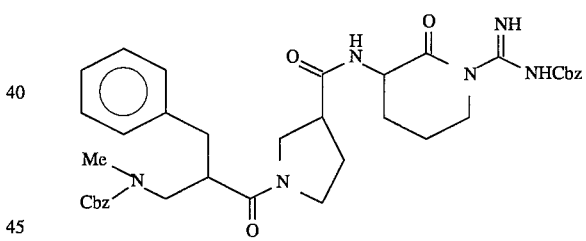

By substantially following the procedures of Example 1,D, 9.0 g (17.5 mmol) of N-methyl-N-Cbz-3-amino-3-phenyl propionyl-L-Pro-benzyl ester was hydrolyzed to afford 7.19 g of the corresponding acid. The presence of the desired product was confirmed by FD-MS (m/e 425; MH$^+$, 100) and the crude mixture was coupled to the Cbz-protected Arg-lactam (6.05 g; 16.67 mmol). The crude product was purified by flash chromatography (SiO$_2$; 75% EtOAc in CH$_2$Cl$_2$) to afford 5.71 g (8.2 mmol 47% from N-methyl-N-Cbz-3-amino-3-phenyl propionyl-L-Pro-benzyl ester) of N-methyl-N-Cbz-3-amino-2-benzylpropionyl-L-Pro-Arg-N-Cbz lactam.
FD-MS, m/e 698 (M+2, 100).
IR (CHCl$_3$) 3376, 3012, 1699, 1615, 1498, 1267, 1181 cm$^{-1}$.
Analytical Calculated for $C_{38}H_{44}N_6O_7$: C 65.50, H 6.36, N 12.06
Found: C 65.31, H 6.39, N 12.08
$[\alpha]_D = -36.3°$ (c=0.01, CH$_2$Cl$_2$).

F. N-methyl-3-amino-2-benzylpropionyl-L-Pro-L-Arg Aldehyde dihydrochloride monohydrate

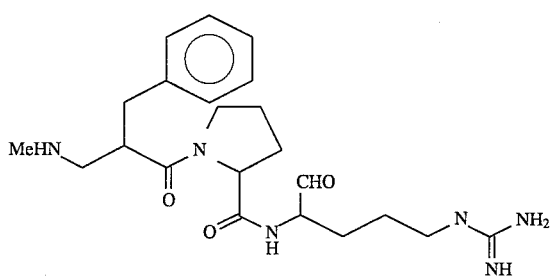

By substantially following the procedures of Example 1,E, 5.65 g (8.1 mmol) of N-methyl-N-Cbz-3-amino-2-benzylpropionyl-L-Pro-Arg-N-Cbz-lactam was reduced with lithium tri-t-butoxyaluminum hydride to afford 4.71 g of the crude protected arginal. Deprotection, again substantially according to the procedures of Example 1.E. gave 2.45 g of crude N-methyl- 3-amino-2-benzylpropionyl-L-Pro-L-Arg aldehyde. Purification by reverse phase chromatography yielded 1.51 g (2.9 mmol; 36% over two steps) of N-methyl-3-amino-2-benzylpropionyl-L-Pro-L-Arg aldehyde as the dihydrochloride monohydrate.
FAB-MS, m/e 431 (MH$^+$; 100).
IR (KBr) 3390, 1653, 1453, 754 cm$^{-1}$.
Analytical Calculated for $C_{22}H_{34}N_6O_3 \cdot 2HCl \cdot H_2O$: C 50.67, H 7.34, N 16.11
Found: C 50.52, H 7.24, N 15.97
$[\alpha]_D=-103.8°$ (c=0.01, MeOH).

EXAMPLE 4

Preparation of 2-(2-Piperidino)acetyl-L-Pro-L-Arginine Aldehyde Dihydrochloride Monohydrate.

A. N-Cbz-2-(2-piperidino) acetic acid

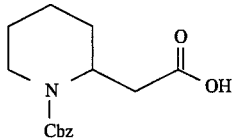

A solution of 24.5 g (140 mmol) of 2-pyridylacetic acid in 470 mL of EtOH was charged with 5.0 g of $PtO_2$ and the mixture hydrogenated at 60 psi for 6 hr at 40° C. The reaction was filtered through Celite® and evaporated to give 29.72 g of a grey oil. The presence of the saturated acid was confirmed by FD-MS (m/e 144; M$^+$1, 100) and the crude reaction mixture was treated with benzylchloroformate (56.45 g; 332 mmol) under basic conditions substantially according to the procedures of Example 1,A, to afford 21.92 g (79.1 mmol; 56% of N-Cbz-2-piperidinoacetic acid as a clear oil.
FD-MS, m/e 277 (M$^+$, 100).
IR (CHCl$_3$) 3011, 2947, 1714, 1690, 1428, 1265, cm$^{-1}$.
Analytical Calculated for $C_{15}H_{19}NO_4$: C 64.97, H 6.91, N 5.05
Found: C 65.20, H 6.88, N 5.34

B. N-Cbz-2-(2-piperidino)acetyl-L-pro-benzyl ester

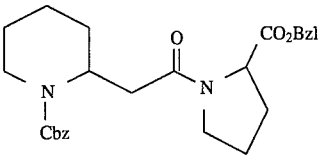

By substantially following the procedures of Example 1,C, 20.85 g (75 mmol) of N-Cbz-2-(2-piperidino)acetic acid was coupled to proline benzylester. The crude product was purified by flash chromatography (SiO$_2$; 10% EtOAc in CH$_2$Cl$_2$) to give 27.61 g (59.6 mmol; 79%) of N-Cbz-2-(2-piperidino)acetyl-L-Pro-benzyl ester as a clear oil.
FD-MS, m/e 464 (M$^+$; 100)
IR (CHCl$_3$) 3013, 1742, 1685, 1425, 1263, 1172 cm$^{-1}$.
Analytical Calculated for $C_{27}H_{32}N_2O_5$: C 69.81, H 6.94, N 6.03
Found: C 69.82, H 7.10, N 6.02
$[\alpha]_D=-40.0°$ (c=0.01, MeOH).

C. N-Cbz-2-(2-piperidino)acetyl-L-Pro-Arg-N-Cbz-lactam

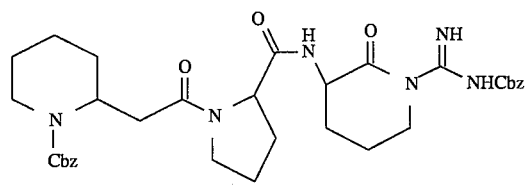

By substantially following the procedures of Example 1,D, 27.36 g (59 mmol) of N-Cbz-2-(2-piperidino)acetyl-L-Pro-benzyl ester was hydrolyzed to afford 31.40 g of the corresponding acid. The presence of the desired acid was confirmed by FDMS (m/e 375; MH$^+$, 100) and a 12.80 g sample of the crude reaction mixture was coupled to N-Cbz-Arg-lactam (12.44 g; 34 mmol) substantially according to the procedures of Example 1,D. Purification of the crude product by flash chromatography (SiO$_2$; 30% CH$_3$CN in CH$_2$Cl$_2$) afforded 4.27 g (6.5 mmol) of N-Cbz-2-(2-piperidinino)acetyl-L-pro-Arg-N-Cbz lactam.
FD-MS, m/e 647 (MH$^+$, 100).
IR (CHCl$_3$) 3012, 1685, 1615, 1499, 1264, 1179 cm$^{-1}$.
Analytical Calculated for $C_{34}H_{42}N_6O_7$: C 63.14, H 6.55, N 12.99
Found: C 63.41, H 6.71, N 12.75
$[\alpha]_D=-45.3°$ (c=0.01, CH$_2$Cl$_2$).

D. 2-(2-Piperidino)acetyl-L-Pro-L-Arg Aldehyde dihydrochloride monohydrate

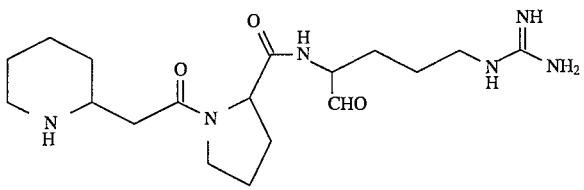

By substantially following the procedures of Example 1,E, 2.60 g (4.2 mmol) of N-Cbz-2-(2-piperdinino)acetyl-L-Pro-Arg-N-Cbz-lactam was reduced with lithium tri-t-butoxyaluminum hydride to afford 2.10 g of the crude protected arginal. Deprotection, again substantially according to the procedures of Example 1,E, afforded 1.13 g (2.49 mmol; 59%) of 2-(2-piperidino)acetyl-L-Pro-L-Arg aldehyde as the dihydrochloride monohydrate.
FAB-MS, m/e 381 (MH$^+$; 100).
IR (KBr) 3336, 2951, 1657, 1453, 1302, 752 cm$^{-1}$.
Analytical Calculated for $C_{18}H_{32}N_6O_3 \cdot 2HCl \cdot H_2O$: C 47.68, H 7.50, N 18.54
Found: C 47.37, H 7.19, N 18.11
$[\alpha]_D = -143.3°$ (c=0.01, MeOH).

EXAMPLE 5

Preparation of 3-piperidinocarbonyl-L-Pro-L-Arginine Aldehyde Dihydrochloride Monohydrate A. N-Cbz-nipecotic acid

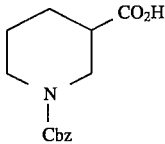

By substantially following the procedures of Example 1,A, 25.0 g (194 mmol) of nipecotic acid was protected with benzylchloroformate under basic conditions to afford 18.0 g (68 mmol; 35%) of analytically pure N-Cbz-nipecotic acid as a white solid.
FD-MS, m/e 264 (MH$^+$, 100).
IR (KBr) 3092, 2950, 1732, 1649, 1449, 1273, 1155, 696 cm$^{-1}$.
Analytical Calculated for $C_{14}H_{17}N_1O_4$: C 63.87, H 6.51, N 5.32
Found: C 63.98, H 6.58, N 5.36

B. N-Cbz-nipecotoyl-L-Pro methyl ester

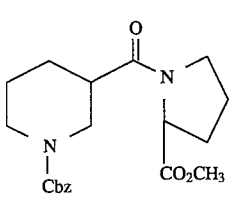

By substantially following the procedures of Example 1,C, 17.0 g (65 mmol) of N-Cbz-nipecotic acid was coupled to proline methyl ester. Purification of the reaction mixture by flash chromatography (SiO$_2$; 70% EtOAc in hexanes) afforded 13.9 g (37.2 mmol; 57%) of N-Cbz-nipecotoyl-L-Pro methyl ester as a clear oil.
FAB-MS, m/e 375 (MH$^+$, 100).
IR (film) 2951, 1746, 1699, 1644, 1426, 1259, 1148, 700 cm$^{-1}$.

Analytical Calculated for $C_{20}H_{26}N_2O_5$: C 64.16, H 7.00, N 7.48
Found: C 64.12, H 7.16, N 7.74

C. N-Cbz-nipecotoyl-L-Pro-Arg-N-Cbz lactam

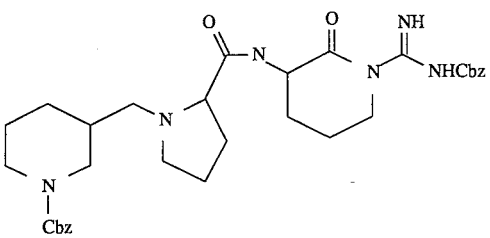

By substantially following the procedures of Example 1,D, 12.9 g (35 mmol) of N-Cbz-nipecotoyl-L-Pro methyl ester was hydrolyzed to afford 10.0 g of the corresponding acid. The presence of the desired product was confirmed by FD-MS (m/e 361; M+1, 100) and the crude reaction mixture was coupled to the Cbz-protected Arg-lactam (10.09 g; 27.8 mmol) again, substantially according to the procedures of Example 1,D. Purification by flash chromatography (SiO$_2$; 50% EtOAc in hexanes) afforded 3.45 g (5.5 mmol; 16% from N-Cbz-nipecotoyl-L-Pro methyl ester) of N-Cbz-nipecotoyl-L-Pro-Arg-N-Cbz lactam.
FD-MS, m/e 633 (MH$^+$, 100).
IR (KBr) 3370, 1700, 1641, 1612, 1264, 1150, 698 cm$^{-1}$.
Analytical Calculated for $C_{33}H_{40}N_6O_7$: C 62.65, H 6.37, N 13.28
Found: C 62.72, H 6.50, N 13.01
$[\alpha]_D = -53.8°$ (c=0.01, MeOH).

D. Nipecotoyl-L-Pro-L-Arg Aldehyde

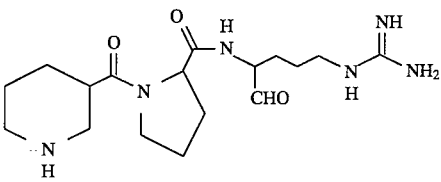

By substantially following the procedures of Example 1,E, 3.0 g (4.7 mmol) of N-Cbz-nipecotoyl-L-Pro-Arg-N-Cbz-lactam was reduced with lithium tri-g-butoxyaluminum hydride to afford 0.75 g of the crude protected arginal. Deprotection by substantially following the procedures of Example 1,E followed by reverse phase chromatography of the crude product yielded 0.13 g (0.2 mmol; 5%) of 3-piperidinocarbonyl-L-Pro-L-Arg aldehyde as the dihydrochloride monohydrate.
FAB-MS, m/e 367 (M$^+$; 100).
IR (KBr) 3336, 2951, 1657, 1453, 1302, 752 cm$^{-1}$.
Analytical Calculated for $C_{18}H_2N_6O_3 \cdot 2HCl \cdot H_2O$: C 47.68, H 7.50, N 18.54
Found: C 47.37, H 7.19, N 18.11
$[\alpha]_D = -32.2°$ (c=0.01, MeOH).

EXAMPLE 6

Preparation of 3-perhydroindolylcarbonyl-L-Pro-L-Arginine Aldehyde Dihydrochloride Monohydrate A. N-Cbz-3-perhydroindolylcarboxylic acid

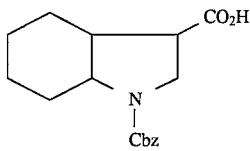

A solution of 25 g (155 mmol) of indole-3-carboxylic acid in 1500 mL $H_2O$ and 150 mL HOAc was charged with 25 g of 5% $Rh/Al_2O_3$ and the mixture hydrogenated at 60 psi for 30 hr at 60° C. The mixture was filtered through Celite® and evaporated in vacuo to a dark oil which was treated with benzylchloroformate (26.35 g; 155 mmol) under basic conditions substantially according to the procedures of Example 1,A. The crude product crystallized out of hot $CH_2Cl_2$/hexanes to yield 16.06 g (53 mmol; 49%) of N-Cbz-3-perhydroindolylcarboxylic acid as a white solid.
FD-MS, m/e 303 ($M^+$; 100)
IR ($CHCl_3$) 3012, 2942, 1698, 1414, 1305, 1117 $cm^{-1}$.
Analytical Calculated for $C_{17}H_{21}NO_4$: C 67.31, H 6.98, N 4.62
Found: C 67.61 H 6.99, N 4.72

B. N-Cbz-3-perhydroindolylcarbonyl-L-Pro-benzyl ester

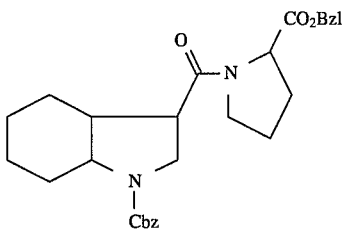

By substantially following the procedures of Example 1,C, 14.03 g (46.3 mmol) of N-Cbz-3-perhydroindolylcarboxylic acid was coupled to proline benzylester to give 22.6 g of crude coupled product. Purification by flash chromatography ($SiO_2$; 10% EtOAc in $CH_2Cl_2$) afforded 18.79 g (38.3 mmol; 83%) of N-Cbz-3 -perhydroindolylcarbonyl-L-pro-benzyl ester as a clear oil.
FD-MS, m/e 490 ($M^+$; 100)
IR ($CHCl_3$) 3013, 2942, 1741, 1694, 1644, 1413, 1174 $cm^{-1}$.
Analytical Calculated for $C_{29}H_{34}N_2O_5$: C 71.00, H 6.98, N 5.71
Found: C 71.10, H 7.12, N 5.77
$[\alpha]_D$=–52.9° (c=0.01, MeOH).

C. N-Cbz-3 -perhydroindolylcarbonyl-L-Pro-Arg-N-Cbz-lactam

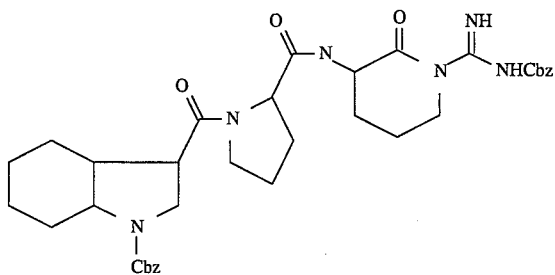

By substantially following the procedures of Example 1,D, 7.54 g (15.39 mmol) of N-Cbz-3-perhydroindolylcarbonyl-L-Pro benzyl ester was hydrolyzed to afford 5.45 g of the corresponding acid. The presence of the desired product was confirmed by FD-MS (m/e 400; $M^+$, 100) and the crude material was coupled to the CBZ-protected Arg-lactam (4.76 g; 13.12 mmol). The product was purified by flash chromatography ($SiO_2$; 75% EtOAc in $CH_2Cl_2$) to afford 4.30 g (6.4 mmol; 42% from N-Cbz-3 -perhydroindolylcarbonyl-L-pro-benzyl ester) of N-Cbz-3 -perhydroindolylcarbonyl-L-pro-Arg-N-Cbz lactam.
FD-MS, m/e 673 ($MH^+$, 100).
IR ($CHCl_3$) 3011, 1687, 1616, 1499, 1268, 1181, 1108 $cm^{-1}$.
Analytical Calculated for $C_{36}H_{44}N_6O_7$: C 64.27, H 6.59, N 12.49
Found: C 64.00, H 6.61, N 12.19
$[\alpha]_D$=–59.2° (c=0.01, $CH_2Cl_2$).

D. 3-perhydroindolylcarbonyl-L-Pro-L-Arg Aldehyde

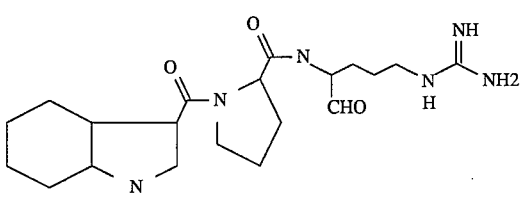

By substantially following the procedures of Example 1,E, 4.08 g (6.16 mmol) of N-Cbz-3-perhydroindolylcarbonyl-L-Pro-Arg-N-Cbz-lactam was reduced with lithium tri-t-butoxyaluminum hydride to afford 2.31 g of the crude protected arginal. Deprotection, again substantially according to Example 1,E, afforded 1.30 g (2.71 mmol; 44% from N-Cbz-3 -perhydroindolylcarbonyl-L-Pro-Arg-N-Cbz-lactam) of analytically pure 3-perhydroindolylcarbonyl-L-Pro-L-Arg Aldehyde as the dihydrochloride monhydrate.
FAB-MS, m/e 407 ($M^+$; 100).
IR (KBr) 3351, 2939, 1658, 1449 $cm^{-1}$.
Analytical Calculated for $C_{20}H_{34}N_6O_3 \cdot 2HCl \cdot 1H_2O$: C 48.30, H 7.69, N 16.89
Found: C 48.72, H 7.41, N 17.01
$[\alpha]_D$=–61.8° (c=0.01, MeOH).

EXAMPLE 7

Preparation of 2-(N-methyl)aminocyclohexyl-carbonyl-L-Pro-L-Arginine Aldehyde Dihydrochloride

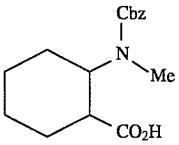

A. 2-(N-methyl-N-Cbz-amino)cyclohexanoic acid

A solution of 50 g (331 mmol) of N-methyl anthranilic acid in $H_2O$ was charged with $RuO_2$ and the mixture hydrogenated at 2000 psi for 10 hrs at 120° C. The catalyst was filtered and the reaction concentrated in vacuo to give 47.2 g of a viscous oil. The oil was taken up in 500 mL of 2N aq NaOH and was washed with $CH_2Cl_2$ (2×250 mL). The basic aqueous layer was treated with benzylchloroformate (56.47 g; 331 mmol) substantially according to the procedures of Example 1,A to afford 50.03 g of crude 2-(N-methyl-N-Cbz-amino)cyclohexanoic acid. The presence of the desired product was confirmed by FDMS (m/e 291, $MH^+$, 100) and the crude product taken on directly to the next step.

B. 2-(N-methyl-N-Cbz-amino)cyclohexylcarbonyl-L-Pro-benzyl ester (7A) and 2-(N-Cbz-amino)cyclohexylcarbonyl-L-Pro-benzyl ester (7B)

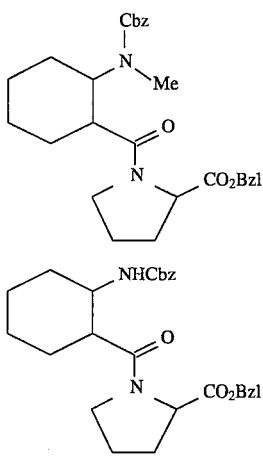

A 24.64 g sample of 2-(N-methyl-N-Cbz-amino)cyclohexanoic acid was coupled to proline benzyl ester (20.49 g; 85 mmol) substantially according to the procedures of Example 1,C. The crude reduction product was purified by flash chromatography (SiO$_2$; 25% EtOAc in hexanes) to afford 22.70 g (47.5 mmol) of 2-(N-methyl-N-Cbz-amino)cyclohexylcarbonyl-L-Pro-benzyl ester and 5.37 g (11.6 mmol) of 2-(N-Cbz-amino)cyclohexylcarbonyl-L-Pro-benzyl ester.

2-(N-methyl-N-Cbz-amino) cyclohexylcarbonyl-L-Pro-benzyl ester:
FD-MS, m/e 478 (M$^+$; 100).
IR (CHCl$_3$) 3013, 2938, 1742, 1683, 1637, 1450, 1347, 1155 cm$^{-1}$.
Analytical Calculated for C$_{28}$H$_{34}$N$_2$O$_5$: C 70.27, H 7.16, N 5.85
Found: C 70.39, H 7.38, N 5.74
[α]$_D$=−10.9° (c=0.01, MeOH).
2-(N-Cbz-amino)cyclohexylcarbonyl-L-Pro-benzyl ester:
FD-MS, m/e 464 (M$^+$; 100).
IR (CHCl$_3$) 3011, 2941, 1741, 1691, 1449, 1173 cm$^{-1}$.
Analytical Calculated for C$_{27}$H$_{32}$N$_2$O$_5$: C 69.81, H 6.94, N 6.03
Found: C 69.55, H 7.16, N 5.91
[α]$_D$=−41.6° (c=0.01, MeOH).
C. 2-(N-methyl-N-Cbz-amino)cyclohexylcarbonyl-L-Pro-L-Arg-N-Cbz-lactam

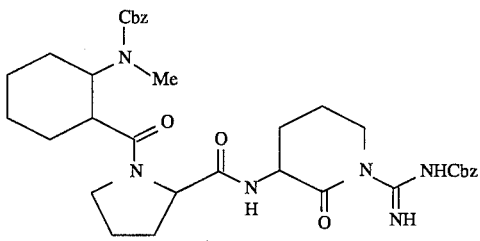

A 22.55 g (47 mmol) sample of 2-(N-methyl-N-Cbz-amino)cyclohexylcarbonyl-L-Pro-benzyl ester was hydrolyzed substantially according to the procedures of Example 1,D, to afford 18.90 g of the crude acid. The presence of the desired product was confirmed by FD-MS (m/e 389, M$^+$1, 100) and the crude material was coupled to CBZ-protected Arg-lactam (17.29 g; 47 mmol), again by substantially the same procedures of Example 1,D. The product was purified by flash chromatography (SiO$_2$; 30% CH$_3$CN in CH$_2$Cl$_2$) to afford 12.20 g (33.6 mmol; 72% from 2-(N-methyl-N-Cbz-amino)cyclohexylcarbonyl-L-Pro-benzyl ester) of 2-(N-methyl-N-Cbz-amino) cyclohexylcarbonyl-L-Arg-N-Cbz-lactam.
FD-MS, m/e 661 (MH$^+$, 100).
IR (CHCl$_3$) 3375, 2941, 1683, 1615, 1498, 1149, 1105 cm$^{-1}$.
Analytical Calculated for C$_{35}$H$_{44}$N$_6$O$_7$: C 63.62, H 6.71, N 12.72
Found: C 63.67, H 6.80, N 12.98
[α]$_D$=−31.4° (c=0.01, CH$_2$Cl$_2$ ).
D. 2-(N-methyl-amino)cyclohexylcarbonyl-L-Pro-L-Arg Aldehyde Dihydrochloride

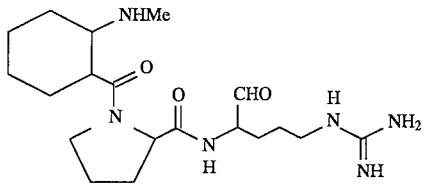

By substantially following the procedures of Example 1,E, 7.90 g (11.97 mmol) of 2 -(N-methyl-N-Cbz-amino)cyclohexylcarbonyl-L-pro-L-Arg-N-Cbz-lactam was reduced with lithium tri-t-butoxyaluminum hydride to afford 5.40 g of the crude protected arginal. Deprotection substantially according to the procedures of Example 1,E, afforded 2.84 g (6.08 mmol; 51% from 2 -(N-methyl-N-Cbz-amino)cyclohexylcarbonyl-L-Pro-L-Arg-N-Cbz-lactam) of analytically pure 2-(N-methylamino)cyclohexylcarbonyl-L-pro-L-Arg aldehyde as the dihydrochloride salt.
FAB-MS, m/e 395 (MH$^+$; 100).
IR (KBr) 3318, 1659, 1456, 1363 cm$^{-1}$.
Analytical Calculated for C$_{19}$H$_{34}$N$_6$O$_3$·2HCl; C 48.82, H 7.76, N 17.98
Found: C 48.54, H 7.63, N 17.83
[α]$_D$=−71.6° (c=0.01, MeOH).

EXAMPLE 8

Preparation of 2-aminocyclohexylcarbonyl-L-Pro-L-Arginine Aldehyde Trihydrochloride Monohydrate
A. 2-(N-Cbz-amino)cyclohexylcarbonyl-L-Pro-Arg-N-Cbz-lactam

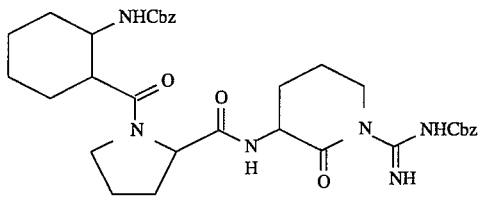

A 5.09 g (10.6 mmol) sample of 2 -(N-Cbz-amino)cyclohexylcarbonyl-L-pro-benzyl ester was hydrolyzed substantially according to the procedures of Example 1,D, to afford 4.34 g of the crude acid. The presence of the desired product was confirmed by FD-MS (m/e 375, MH$^+$, 100) and the crude material was coupled to CBZ-protected Arg-lactam (4.02 g; 11.1 mmol) by substantially the same procedures of Example 1,D. The product was purified by flash chromatography (SiO$_2$; 30% CH$_3$CN in CH$_2$Cl$_2$) to afford 1.46 g (2.21 mmol; 20% from 2 -(N-Cbz-amino)cyclohexylcarbonyl-L-pro-benzyl ester) of 2 -(N-Cbz-amino)cyclohexylcarbonyl-L-pro-Arg-N-Cbz-lactam.
FD-MS, m/e 647 (MH$^+$, 100).

IR (CHCl$_3$) 3376, 2943, 1703, 1616, 1509, 1267, 1181, 1043 cm$^{-1}$.
Analytical Calculated for C$_{34}$H$_{42}$N$_6$O$_7$: C 63.14, H 6.55, N 12.99
Found: C 63.23, H 6.47, N 12.79
$[\alpha]_D$=–43.7° (c=0.01, CH$_2$Cl$_2$ ).

B. 2-Aminocyclohexylcarbonyl-L-Pro-L-Arg Aldehyde

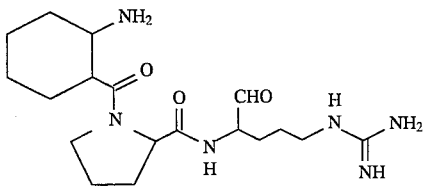

By substantially following the procedures of Example 1,E, 1.28 g (1.94 mmol) of 2-(N-Cbz-amino)cyclohexylcarbonyl-L-Pro-Arg-N-Cbz-lactam was reduced with lithium tri-t-butoxyaluminum hydride to afford 0.82 g of the crude protected arginal. Deprotection, again substantially according to the procedures of Example 1,E, afforded 0.40 g (0.88 mmol; 46% from 2-(N-Cbz-amino)cyclohexylcarbonyl-L-Pro-Arg-N-Cbz-lactam) of analytically pure 2-aminocyclohexylcarbonyl-L-Pro-L-Arg Aldehyde as the trihydrochloride monohydrate.
FAB-MS, m/e 381 (M$^+$; 100).
IR (KBr) 3330, 1663, 1451, 1002 cm$^{-1}$.
Analytical Calculated for C$_{19}$H$_{34}$N$_6$O$_3$·3HCl·H$_2$O: C 48.82, H 7.76, N 17.98
Found: C 48.54, H 7.63, N 17.83
$[\alpha]_D$=–74.5° (c=0.01, MeOH).

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases and disorders where blood coagulation could be a fundamental contributing process or a source of secondary pathology, such as cancer, including metastasis, inflammatory diseases, including arthritis, and diabetes. The anti-coagulant compound is administered orally or parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regime may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (tPA), modified tPA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9%), 5% dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl- pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The compounds provided by the invention (formula 1) selectively inhibit the action of thrombin in mammals.

The ability of the compounds of the present invention to be an effective thrombin inhibitor is evaluated in one or more of the following assays.

The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-Phe-Val-Arg-p-nitroanilide.

The assay is carried out by mixing 50 µl buffer (0.03M Tris, 0.15M NaCl, pH 7.4) with 25 µl of human thrombin solution (purified human thrombin, Enzyme Research Laboratories, South Bend, Ind., at 8 NIH units/ml) and 25 µl of test compound in a solvent (50% aqueous methanol (v:v)). Then 150 µl of an aqueous solution of the chromogenic substrate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

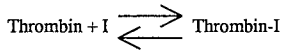

$$Kass = \frac{[Thrombin\ I]}{[(Thrombin) \times (I)]}$$

Kass is calculated for a range of concentrations of test compounds and the mean value reported in units of liter per mole.

By substantially following the procedures described above for human thrombin, and using other human blood coagulation system serine proteases, and using fibrinolytic system serine proteases with the chromogenic substrates, indentified below, the selectivity of the compounds of the present invention with respect to the coagulation factor serine proteases and to the fibrinolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952 incorporated by reference herein in its entirety. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from KabiVitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and t-PA substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by the formula 1.

TABLE 1

| Human Thrombin Inhibition Levels | |
|---|---|
| Example | Kass × $10^6$ (l/mole) |
| 1 | 70 |
| 2 | 85 |
| 3 | 12 |
| 4 | 1 |
| 5 | 2 |
| 6 | 11 |
| 7 | 18.4 |
| 8 | 39 |

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic protease), such fibronolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Plough units/vial. Streptokinase is purchased from Hoechst Pharmaceuticals, Somerville, N.J.

Methods—Effects on Lysis of Human Plasma clots by t-PA

Human plasma clots are formed in micro test tubes by adding 50 ul thrombin (73 NIH unit/ml) to 100 ul human plasma which contains 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of IC50 values are estimated by linear extrapolations from data points to a value which would represent 50 percent of lysis for that particular concentration of fibrinolytic agent.

Anticoagulant Activity

Materials

Dog plasma and rat plasma is obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis Detroit, Mich., is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 ml saline and 0.05 ml Thromboplastin-C reagent to 0.05 ml test plasma. The activated partial thromboplastin time (APTT) is measured by incubation of 0.05 ml test plasma with 0.05 ml Actin reagent for 120 seconds followed by 0.05 ml CaCl2 (0.02M). The thrombin time (TT) is measured by adding 0.05 ml saline and 0.05 ml thrombin (10 NIH units/ml) to 0.05 ml test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29,1982).

FeCl$_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20%) is expressed in terms of the actual weight of $FeCl_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269,1990).

Spontaneous thrombolysis model

In vitro data suggests that peptide thrombin inhibitors inhibit thrombin and at higher concentrations may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}I$ human fibrogen (5 μCi, ICN), immediately drawn into silastic tubing and incubated at 37° C. for 1 hr. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika) are incubated for 5 minutes (37° C.) and $CaCl_2$ (0.01 ml, 0.025M) is added to start coagulation. Assays are done in duplicate and averaged.

Index of Bioavailability

A measure of bioactivity, plasma thrombin time (TT), serves as a substitute for the assay of parent compound on the assumption that increments in TT results from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC \text{ po}}{AUC \text{ iv}} \times \frac{\text{Dose iv}}{\text{Dose po}} \times 100$$

Compounds

Compound solutions are prepared fresh daily in normal saline and are injected as a bolus or are infused starting 15 min before and continuing throughout the experimental perturbation which is 15 minutes in the arteriovenous shunt model of arterial injury and 60 minutes in the $FeCl_3$ model of areterial injury and in the spontaneous thrombolysis model. Bolus injection volume is 1 ml/kg for i.v., and 5 ml/kg for p.o. and infusion volume is 3 ml/hr.

Statistics

Results are expressed as means +/− SEM. One-way analysis of variance is used to detect statistically significant differences and then Dunnett's test is applied to determine which means are different. Significance level for rejection of the null hypothesis of equal means is $P<0.05$.

TABLE 2

Index of Bioavailability

| Example | Percent Relative Activity |
|---|---|
| 1 | 28 |
| 2 | 19 |
| 3 | 8 |
| 8 | 15 |

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50% relative humidity; and lighted from 0600–1800 hours.

Pharmacokinetic model.

Test compound is formulated immediately prior to dosing by dissolving in sterile 0.9% saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH7 with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound at Tmax, Cmax; plasma half-life, t0.5; area under the curve, A.U.C.; and fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound. A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50% inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 h. A 2-h infusion of the compounds of the present invention at doses of 0.5 and 1 mg/kg/h is begun simultaneously with an infusion of thrombolytic agent (e.g. tissue plasminogen activator, streptokinase, APSAC). Reperfusion is followed for 3h after administration of test compound. Reocclusion of coronary arteries after successful thrombolysis is defined as zero CBF which persisted for ≧30 min.

Hematology and template bleeding time determinations

Whole blood cell counts, hemoglobin, and hematocrit values are determined on a 40-µl sample of citrated (3.8%) blood (1 part citrate:9 parts blood) with a hematology analyzer (Cell-Dyn 900, Sequoia-Turner. Mount View, Calif., U.S.A.). Gingival template bleeding times are determined with a Simplate II bleding time device (Organon Teknika Durham, N.C., U.S.A.). The device is used to make 2 horizontal incisions in the gingiva of either the upper or lower left jaw of the dog. Each incision is 3 mm wide ×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean ±SEM. All studies are conducted in accordance with the guiding principles of the American Physiological Society. Further details regarding the procedures are described in Jackson, et el., *J. Cardiovasc. Pharmacol.*, 21, 587–599 (1993).

We claim:

1. A compound having the formula

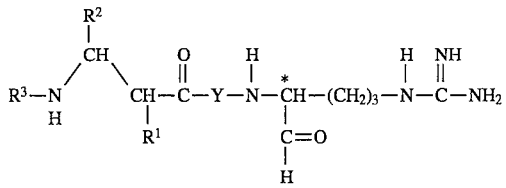

wherein $R^1$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–$C_4$)alkyl, or cyclohexyl($C_1$–$C_4$)alkyl;

$R^2$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–$C_4$)alkyl or cyclohexyl($C_1$–$C_4$)alkyl;

$R^3$ is hydrogen, $C_1$–$C_4$ alkyl or ($C_1$–$C_4$ alkyl)S(O)$_n$ where n is 1 or 2;

$R^1$ and $R^2$, with the carbon atoms to which they are bonded, are combined to afford a 5 or 6 membered cycloalkyl group, a phenyl group or norbornanyl group;

$R^2$ and $R^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

$R^1$, $R^2$ and $R^3$, with the respective carbon and nitrogen atoms to which they are bonded, are combined to afford an unsubstituted or substituted 5 or 6 membered nitrogen containing heterocyclic ring or an unsubstituted or substituted 9 or 10 membered nitrogen containing heterocyclic ring which may further contain another hetero atom selected from nitrogen, oxygen and sulfur;

Y is

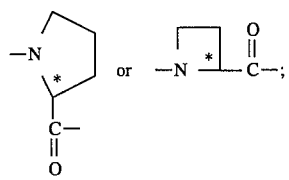

or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl; and further provided that $R^3$ is not hydrogen or ($C_1$–$C_4$ alkyl)S(O)$_n$ when $R_1$ and $R_2$ are each hydrogen.

2. A compound of claim 1 where

R$^1$ is hydrogen, phen(C$_1$–C$_4$) alkyl, or cyclohexyl(C$_1$–C$_4$)alkyl;

R$^2$ is hydrogen, cyclopentyl, cyclohexyl or phenyl;

R$^3$ is hydrogen or C$_1$–C$_4$ alkyl; or

R$^1$ and R$^2$, with the carbon atoms to which they are bonded, are combined to afford a 5 or 6 membered cycloalkyl group; or R$^1$, R$^2$ and R$^3$, with the respective carbon and nitrogen atoms to which they are bonded, are combined to afford an unsubstituted or substituted 9 or 10 membered nitrogen containing heterocyclic ring;

Y is prolinyl or azetidinyl-2-carbonyl, or pharmaceutically acceptable salts and solvates thereof; provided that when Y is prolinyl, R$^1$ is hydrogen and R$^3$ is hydrogen, R$^2$ is not phenyl; and further provided that when Y is prolinyl, R$^2$ is hydrogen and R$^3$ is hydrogen, R$^1$ is not benzyl.

3. A compound of claim 2 where

R$^1$ is hydrogen, benzyl or cyclohexylmethyl;

R$^2$ is hydrogen, cyclohexyl or phenyl;

R$^3$ is hydrogen or C$_1$–C$_3$ alkyl; or

R$^1$ and R$^2$, with the carbon atoms to which they are bonded, are combined to afford a 5 or 6 membered cycloalkyl group;

Y is prolinyl or azetidinyl-2-carbonyl, or pharmaceutically acceptable salts and solvates therof; provided that when Y is prolinyl, R$^1$ is hydrogen and R$^3$ is hydrogen, R$^2$ is not phenyl; and further provided that when Y is prolinyl, R$^2$ is hydrogen and R$^3$ is hydrogen, R$^1$ is not benzyl.

4. A compound of claim 3 which is N-methyl-3-amino-3-phenylpropionyl-L-prolinyl-L-arginine aldehyde or pharmaceutically acceptable salts and solvates thereof.

5. A compound of claim 3 which is N-methyl-3-amino-3-cyclohexylpropionyl-L-prolinyl-L-arginine aldehyde or pharmaceutically acceptable salts and solvates thereof.

6. A compound of claim 3 which is 2-aminocyclohexylcarbonyl-L-prolinyl-L-arginine aldehyde or pharmaceutically acceptable salts and solvates thereof.

7. A pharmaceutical formulation comprising in association with a pharmaceutically acceptable carrier, diluent, or excipient, a compound of the formula

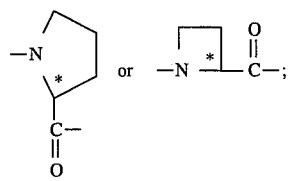

wherein

R$^1$ is hydrogen, C$_1$–C$_4$ alkyl, substituted or unsubstituted phenyl, substituted or unsubstituted phen(C$_1$–C$_4$)alkyl, cyclopentyl, cyclohexyl, cyclopentyl(C$_1$–C$_4$)alkyl, or cyclohexyl(C$_1$–C$_4$)alkyl;

R$^2$ is hydrogen, C$_1$–C$_4$ alkyl, substituted or unsubstituted phenyl, substituted or unsubstituted phen(C$_1$–C$_4$)alkyl, cyclopentyl, cyclohexyl, cyclopentyl(C$_1$–C$_4$)alkyl or cyclohexyl(C$_1$–C$_4$)alkyl;

R$^3$ is hydrogen, C$_1$–C$_4$ alkyl or (C$_1$–C$_4$ alkyl)S(O)$_n$ where n is 1 or 2;

R$^1$ and R$^2$, with the carbon atoms to which they are bonded, are combined to afford a 5 or 6 membered cycloalkyl group, a phenyl group or norbornanyl group;

R$^2$ and R$^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

R$^1$, R$^2$ and R$^3$, with the respective carbon and nitrogen atoms to which they are bonded, are combined to afford an unsubstituted or substituted 5 or 6 membered nitrogen containing heterocyclic ring or an unsubstituted or substituted 9 or 10 membered nitrogen containing heterocyclic ring which may further contain another hetero atom selected from nitrogen, oxygen and sulfur;

Y is

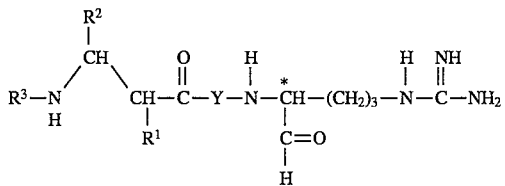

or pharmaceutically acceptable salts and solvates thereof; provided that when Y is prolinyl, R$^1$ is hydrogen and R$^3$ is hydrogen, R$^2$ is not phenyl; and further provided that when Y is prolinyl, R$^2$ is hydrogen and R$^3$ is hydrogen, R$^1$ is not benzyl; and further provided that R$^3$ is not hydrogen or (C$_1$–C$_4$ alkyl)S(O)$_n$ when R$_1$ and R$_2$ are each hydrogen.

8. A formulation of claim 7 where

R$^1$ is hydrogen, phen(C$_1$–C$_4$) alkyl, or cyclohexyl(C$_1$–C$_4$)alkyl;

R$^2$ is hydrogen, cyclopentyl, cyclohexyl or phenyl;

R$^3$ is hydrogen or C$_1$–C$_4$ alkyl; or

R$^1$ and R$^2$, with the carbon atoms to which they are bonded, are combined to afford a 5 or 6 membered cycloalkyl group; or R$^1$, R$^2$ and R$^3$, with the respective carbon and nitrogen atoms to which they are bonded, are combined to afford an unsubstituted or substituted 9 or 10 membered nitrogen containing heterocyclic ring;

Y is prolinyl or azetidinyl-2-carbonyl, or pharmaceutically acceptable salts and solvates thereof; provided that when Y is prolinyl, R$^1$ is hydrogen and R$^3$ is hydrogen, R$^2$ is not phenyl; and further provided that when Y is prolinyl, R$^2$ is hydrogen and R$^3$ is hydrogen, R$^1$ is not benzyl.

9. A formulation of claim 8 where

R$^1$ is hydrogen, benzyl or cyclohexylmethyl;

R$^2$ is hydrogen, cyclohexyl or phenyl;

R$^3$ is hydrogen or C$_1$–C$_3$ alkyl; or

R$^1$ and R$^2$, with the carbon atoms to which they are bonded, are combined to afford a 5 or 6 membered cycloalkyl group;

Y is prolinyl or azetidinyl-2-carbonyl, or pharmaceutically acceptable salts and solvates therof; provided that when Y is prolinyl, R$^1$ is hydrogen and R$^3$ is hydrogen, R$^2$ is not phenyl; and further provided that when Y is prolinyl, R$^2$ is hydrogen and R$^3$ is hydrogen, R$^1$ is not benzyl.

10. A formulation of claim 9 where said compound is N-methyl-3-amino-3-phenylpropionyl-L-prolinyl-L-arginine aldehyde or pharmaceutically acceptable salts and solvates thereof.

11. A formulation of claim 9 where said compound is N-methyl-3-amino-3-cyclohexylpropionyl-L-prolinyl-L-arginine aldehyde or pharmaceutically acceptable salts and solvates thereof.

12. A formulation of claim 9 where said compound is 2-aminocyclohexylcarbonyl-L-prolinyl-L-arginine aldehyde or pharmaceutically acceptable salts and solvates thereof.

13. A method of inhibiting thrombin in mammals, comprising administering to a mammal requiring thrombin inhibition, on effective dose of a compound having the formula

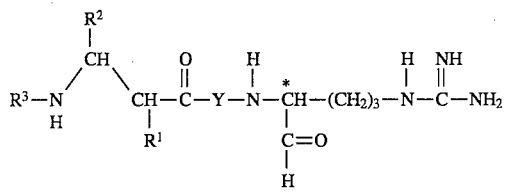

wherein $R^1$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–C4)alkyl, or cyclohexyl($C_1$–$C_4$)alkyl;

$R^2$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–$C_4$)alkyl or cyclohexyl($C_1$–$C_4$)alkyl;

$R^3$ is hydrogen, $C_1$–$C_4$ alkyl or ($C_1$–$C_4$ alkyl)S(O)$_n$ where n is 1 or 2;

$R^1$ and $R^2$, with the carbon atoms to which they are bonded, are combined to afford a 5 or 6 membered cycloalkyl group, a phenyl group or norbornanyl group;

$R^2$ and $R^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

$R^1$, $R^2$ and $R^3$, with the respective carbon and nitrogen atoms to which they are bonded, are combined to afford an unsubstituted or substituted 5 or 6 membered nitrogen containing heterocyclic ring or an unsubstituted or substituted 9 or 10 membered nitrogen containing heterocyclic ring which may further contain another hetero atom selected from nitrogen, oxygen and sulfur;

Y is

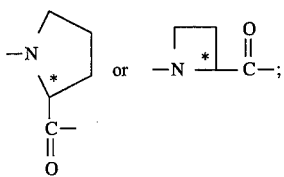

or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl; and further provided that $R^3$ is not hydrogen or ($C_1$–$C_4$ alkyl)S(O)$_n$ when $R_1$ and $R_2$ are each hydrogen.

14. The method of claim 13 where $R^1$ is hydrogen, phen($C_1$–$C_4$) alkyl, or cyclohexyl($C_1$–$C_4$)alkyl;

$R^2$ is hydrogen, cyclopentyl, cyclohexyl or phenyl;

$R^3$ is hydrogen or $C_1$–$C_4$ alkyl; or $R^1$ and $R^2$, with the carbon atoms to which they are bonded, are combined to afford a 5 or 6 membered cycloalkyl group; or $R^1$, $R^2$ and $R^3$, with the respective carbon and nitrogen atoms to which they are bonded, are combined to afford an unsubstituted or substituted 9 or 10 membered nitrogen containing heterocyclic ring;

Y is prolinyl or azetidinyl-2-carbonyl, or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

15. The method of claim 14 where $R^1$ is hydrogen, benzyl or cyclohexylmethyl;

$R^2$ is hydrogen, cyclohexyl or phenyl;

$R^3$ is hydrogen or $C_1$–$C_3$ alkyl; or $R^1$ and $R^2$, with the carbon atoms to which they are bonded, are combined to afford a 5 or 6 membered cycloalkyl group;

Y is prolinyl or azetidinyl-2-carbonyl, or pharmaceutically acceptable salts and solvates therof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

16. The method of claim 15 where said compound is N-methyl-3-amino-3-phenylpropionyl-L-prolinyl-L-arginine aldehyde or pharmaceutically acceptable salts and solvates thereof.

17. The method of claim 15 where said compound is N-methyl-3-amino-3-cyclohexylpropionyl-L-prolinyl-L-arginine aldehyde or pharmaceutically acceptable salts and solvates thereof.

18. The method of claim 15 where said compound is 2-aminocyclohexylcarbonyl-L-prolinyl-L-arginine aldehyde or pharmaceutically acceptable salts and solvates thereof.

19. A method of treating a thromboembolic disorder in mammals, comprising administering to a mammal requiring treatment, an effective dose of a compound having the formula

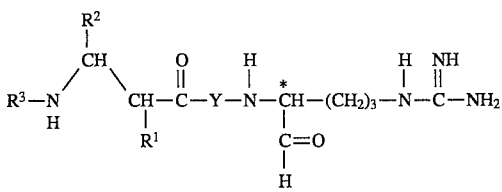

wherein $R^1$ is hydrogen, $C_1$–$C_4$ alkyl, substituted or unsubstituted phenyl, substituted or unsubstituted phen($C_1$–$C_4$)alkyl, cyclopentyl, cyclohexyl, cyclopentyl($C_1$–$C_4$)alkyl, or cyclohexyl($C_1$–$C_4$)alkyl;

43

$R^2$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl or cyclohexyl($C_1$-$C_4$)alkyl;

$R^3$ is hydrogen, $C_1$-$C_4$ alkyl or ($C_1$-$C_4$ alkyl)S(O)$_n$ where n is 1 or 2;

$R^1$ and $R^2$, with the carbon atoms to which they are bonded, are combined to afford a 5 or 6 membered cycloalkyl group, a phenyl group or norbornanyl group;

$R^2$ and $R^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

$R^1$, $R^2$ and $R^3$, with the respective carbon and nitrogen atoms to which they are bonded, are combined to afford an unsubstituted or substituted 5 or 6 membered nitrogen containing heterocyclic ring or an unsubstituted or substituted 9 or 10 membered nitrogen containing heterocyclic ring which may further contain another hetero atom selected from nitrogen, oxygen and sulfur;

Y is $$-N\underset{*}{\overset{\diagup\diagdown}{\phantom{x}}}\underset{\parallel}{\underset{O}{C-}} \quad \text{or} \quad -N\underset{*}{\overset{\square}{\phantom{x}}}\underset{\parallel}{\overset{O}{C-}};$$

or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl; and further provided that $R^3$ is not hydrogen or ($C_1$-$C_4$ alkyl)S(O)$_n$ when $R_1$ and $R_2$ are each hydrogen.

20. The method of claim 19 where $R^1$ is hydrogen, phen($C_1$-$C_4$) alkyl, or cyclohexyl($C_1$-$C_4$)alkyl;

$R^2$ is hydrogen, cyclopentyl, cyclohexyl or phenyl;

$R^3$ is hydrogen or $C_1$-$C_4$ alkyl; or $R^1$ and $R^2$, with the carbon atoms to which they are bonded, are combined to afford a 5 or 6 membered cycloalkyl group; or $R^1$, $R^2$ and $R^3$, with the respective carbon and nitrogen atoms to which they are bonded, are combined to afford an unsubstituted or substituted 9 or 10 membered nitrogen containing heterocyclic ring;

Y is prolinyl or azetidinyl-2-carbonyl, or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

21. The method of claim 20 where $R^1$ is hydrogen, benzyl or cyclohexylmethyl;

$R^2$ is hydrogen, cyclohexyl or phenyl;

$R^3$ is hydrogen or $C_1$-$C_3$ alkyl; or $R^1$ and $R^2$, with the carbon atoms to which they are bonded, are combined to afford a 5 or 6 membered cycloalkyl group;

44

Y is prolinyl or azetidinyl-2-carbonyl, or pharmaceutically acceptable salts and solvates therof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

22. The method of claim 21 where said compound is N-methyl-3-amino-3-phenylpropionyl-L-prolinyl-L-arginine aldehyde or pharmaceutically acceptable salts and solvates thereof.

23. The method of claim 21 where said compound is N-methyl-3-amino-3-cyclohexylpropionyl-L-prolinyl-L-arginine aldehyde or pharmaceutically acceptable salts and solvates thereof.

24. The method of claim 21 where said compound is 2-aminocyclohexylcarbonyl-L-prolinyl-L-arginine aldehyde or pharmaceutically acceptable salts and solvates thereof.

25. A method of inhibiting coagulation in mammals, comprising administering to a mammal requiring coagulation inhibition, an effective dose of a compound having the formula $$R^3-\underset{H}{N}\diagdown\underset{\underset{\displaystyle CH}{|}}{\overset{R^2}{|}}\diagup\underset{\underset{\displaystyle R^1}{|}}{CH}-\overset{O}{\overset{\parallel}{C}}-Y-\underset{H}{N}-\overset{*}{\underset{\underset{\displaystyle C=O}{|}}{CH}}-(CH_2)_3-\underset{H}{N}-\overset{NH}{\overset{\parallel}{C}}-NH_2 \quad \text{I}$$

$$\phantom{xxxxxxxxxxxxxxxxxxxxxxxxxxxxx}\underset{H}{|}$$

wherein $R^1$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl, or cyclohexyl($C_1$-$C_4$)alkyl;

$R^2$ is hydrogen, $C_1$-$C_4$ alkyl, substituted or unsubstituted phenyl, substituted or unsubstituted phen($C_1$-$C_4$)alkyl, cyclopentyl, cyclohexyl, cyclopentyl($C_1$-$C_4$)alkyl or cyclohexyl($C_1$-$C_4$)alkyl;

$R^3$ is hydrogen, $C_1$-$C_4$ alkyl or ($C_1$-$C_4$ alkyl)S(O)$_n$ where n is 1 or 2;

$R^1$ and $R^2$, with the carbon atoms to which they are bonded, are combined to afford a 5 or 6 membered cycloalkyl group, a phenyl group or norbornanyl group;

$R^2$ and $R^3$, with the respective carbon and nitrogen atoms to which they are bonded, are combined to afford an unsubstituted or substituted 5 or 6 membered nitrogen containing heterocyclic ring which may further contain another hetero atom selected from nitrogen, oxygen and sulfur, or unsubstituted or substituted 9 or 10 membered nitrogen containing heterocyclic ring which may further contain another hetero atom selected from nitrogen, oxygen and sulfur;

$R^1$, $R^2$ and $R^3$, with the respective carbon and nitrogen atoms to which they are bonded, are combined to afford an unsubstituted or substituted 5 or 6 membered nitrogen containing heterocyclic ring or an unsubstituted or substituted 9 or 10 membered nitrogen containing heterocyclic ring which may further contain another hetero atom selected from nitrogen, oxygen and sulfur;

Y is

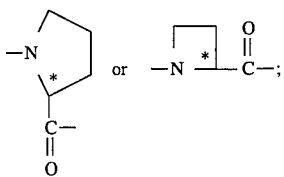

or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl; and further provided that $R^3$ is not hydrogen or $(C_1-C_4$ alkyl$)S(O)_n$ when $R_1$ and $R_2$ are each hydrogen.

26. The method of claim 25 where
  $R^1$ is hydrogen, phen($C_1$–$C_4$) alkyl, or cyclohexyl($C_1$–$C_4$)alkyl;
  $R^2$ is hydrogen, cyclopentyl, cyclohexyl or phenyl;
  $R^3$ is hydrogen or $C_1$–$C_4$ alkyl; or
  $R^1$ and $R^2$, with the carbon atoms to which they are bonded, are combined to afford a 5 or 6 membered cycloalkyl group; or
  $R^1$, $R^2$ and $R^3$, with the respective carbon and nitrogen atoms to which they are bonded, are combined to afford an unsubstituted or substituted 9 or 10 membered nitrogen containing heterocyclic ring;
  Y is prolinyl or azetidinyl-2-carbonyl, or pharmaceutically acceptable salts and solvates thereof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

27. The method of claim 26 where
  $R^1$ is hydrogen, benzyl or cyclohexylmethyl;
  $R^2$ is hydrogen, cyclohexyl or phenyl;
  $R^3$ is hydrogen or $C_1$–$C_3$ alkyl; or
  $R^1$ and $R^2$, with the carbon atoms to which they are bonded, are combined to afford a 5 or 6 membered cycloalkyl group;
  Y is prolinyl or azetidinyl-2-carbonyl, or pharmaceutically acceptable salts and solvates therof; provided that when Y is prolinyl, $R^1$ is hydrogen and $R^3$ is hydrogen, $R^2$ is not phenyl; and further provided that when Y is prolinyl, $R^2$ is hydrogen and $R^3$ is hydrogen, $R^1$ is not benzyl.

28. The method of claim 27 where said compound is N-methyl-3-amino-3-phenylpropionyl-L-prolinyl-L-arginine aldehyde or pharmaceutically acceptable salts and solvates thereof.

29. The method of claim 27 where said compound is N-methyl-3-amino-3-cyclohexylpropionyl-L-prolinyl-L-arginine aldehyde or pharmaceutically acceptable salts and solvates thereof.

30. The method of claim 27 where said compound is 2-aminocyclohexylcarbonyl-L-prolinyl-L-arginine aldehyde or pharmaceutically acceptable salts and solvates thereof.

31. A compound of claim 1 which is selected from the group consisting of:
  a. N-methyl-3-amino-3-phenylpropionyl-L-prolinyl-L-arginine aldehyde,
  b. N-methyl-3-amino-3-cyclohexylpropionyl-L-prolinyl-L-arginine aldehyde,
  c. N-methyl-3-amino-2-benzylpropionyl-L-prolinyl-L-arginine aldehyde,
  d. 2-(2-piperidinyl)acetyl-L-prolinyl-L-arginine aldehyde,
  e. 3-piperidinylcarbonyl-L-prolinyl-L-arginine aldehyde,
  f. 3-perhydroindolylcarbonyl-L-prolinyl-L-arginine aldehyde,
  g. 2-(N-methyl)aminocyclohexyl-carbonyl-L-prolinyl-L-arginine aldehyde,
  h. 2-aminocyclohexylcarbonyl-L-prolinyl-L-arginine aldehyde, or pharmaceutically acceptable salts and solvates thereof.

32. A formulation of claim 7 where said compound is selected from the group consisting of:
  a. N-methyl-3-amino-3-phenylpropionyl-L-prolinyl-L-arginine aldehyde,
  b. N-methyl-3-amino-3-cyclohexylpropionyl-L-prolinyl-L-arginine aldehyde,
  c. N-methyl-3-amino-2-benzylpropionyl-L-prolinyl-L-arginine aldehyde,
  d. 2-(2-piperidinyl)acetyl-L-prolinyl-L-arginine aldehyde,
  e. 3-piperidinylcarbonyl-L-prolinyl-L-arginine aldehyde,
  f. 3-perhydroindolylcarbonyl-L-prolinyl-L-arginine aldehyde,
  g. 2-(N-methyl)aminocyclohexyl-carbonyl-L-prolinyl-L-arginine aldehyde,
  h. 2-aminocyclohexylcarbonyl-L-prolinyl-L-arginine aldehyde, or pharmaceutically acceptable salts and solvates thereof.

33. The method of claim 13 where said compound is selected from the group consisting of:
  a. N-methyl-3-amino-3-phenylpropionyl-L-prolinyl-L-arginine aldehyde,
  b. N-methyl-3-amino-3-cyclohexylpropionyl-L-prolinyl-L-arginine aldehyde,
  c. N-methyl-3-amino-2-benzylpropionyl-L-prolinyl-L-arginine aldehyde,
  d. 2-(2-piperidinyl)acetyl-L-prolinyl-L-arginine aldehyde,
  e. 3-piperidinylcarbonyl-L-prolinyl-L-arginine aldehyde,
  f. 3-perhydroindolylcarbonyl-L-prolinyl-L-arginine aldehyde,
  g. 2-(N-methyl)aminocyclohexyl-carbonyl-L-prolinyl-L-arginine aldehyde,
  h. 2-aminocyclohexylcarbonyl-L-prolinyl-L-arginine aldehyde, or pharmaceutically acceptable salts and solvates thereof.

34. The method of claim 19 where said compound is selected from the group consisting of:
  a. N-methyl-3-amino-3-phenylpropionyl-L-prolinyl-L-arginine aldehyde,
  b. N-methyl-3-amino-3-cyclohexylpropionyl-L-prolinyl-L-arginine aldehyde,
  c. N-methyl-3-amino-2-benzylpropionyl-L-prolinyl-L-arginine aldehyde,
  d. 2-(2-piperidinyl)acetyl-L-prolinyl-L-arginine aldehyde,
  e. 3-piperidinylcarbonyl-L-prolinyl-L-arginine aldehyde,
  f. 3-perhydroindolylcarbonyl-L-prolinyl-L-arginine aldehyde,
  g. 2-(N-methyl)aminocyclohexyl-carbonyl-L-prolinyl-L-arginine aldehyde, h. 2-aminocyclohexylcarbonyl-L-prolinyl-L-arginine aldehyde, or pharmaceutically acceptable salts and solvates thereof.

35. The method of claim 25 where said compound is selected from the group consisting of:

a. N-methyl-3-amino-3-phenylpropionyl-L-prolinyl-L-arginine aldehyde, b. N-methyl-3-amino-3-cyclohexylpropionyl-L-prolinyl-L-arginine aldehyde, c. N-methyl-3-amino-2-benzylpropionyl-L-prolinyl-L-arginine aldehyde, d. 2-(2-piperidinyl)acetyl-L-prolinyl-L-arginine aldehyde, e. 3-piperidinylcarbonyl-L-prolinyl-L-arginine aldehyde, f. 3-perhydroindolylcarbonyl-L-prolinyl-L-arginine aldehyde, g. 2-(N-methyl)aminocyclohexyl-carbonyl-L-prolinyl-L-arginine aldehyde, h. 2-aminocyclohexylcarbonyl-L-prolinyl-L-arginine aldehyde, or pharmaceutically acceptable salts and solvates thereof.

* * * * *